United States Patent
Fleck et al.

(10) Patent No.: US 11,078,182 B2
(45) Date of Patent: Aug. 3, 2021

(54) HETEROAROMATIC COMPOUNDS AS VANIN INHIBITORS

(71) Applicant: Boehringer Ingelheim International GmbH, Ingelheim am Rhein (DE)

(72) Inventors: Martin Thomas Fleck, Munich (DE); Cedrickx Godbout, Attenweiler (DE); Hannes Fiepko Koolman, Biberach (DE)

(73) Assignee: Boehringer Ingelheim International GmbH, Ingelheim am Rhein (DE)

(*) Notice: Subject to any disclaimer, the term of this patent is extended or adjusted under 35 U.S.C. 154(b) by 0 days.

(21) Appl. No.: 16/699,799

(22) Filed: Dec. 2, 2019

(65) Prior Publication Data
US 2020/0172508 A1 Jun. 4, 2020

(30) Foreign Application Priority Data
Dec. 3, 2018 (EP) .................................... 18209721

(51) Int. Cl.
| C07D 401/06 | (2006.01) |
| C07D 401/14 | (2006.01) |
| C07D 405/14 | (2006.01) |
| C07D 413/14 | (2006.01) |
| A61K 45/06 | (2006.01) |

(52) U.S. Cl.
CPC ......... *C07D 401/06* (2013.01); *C07D 401/14* (2013.01); *C07D 405/14* (2013.01); *C07D 413/14* (2013.01); *A61K 45/06* (2013.01)

(58) Field of Classification Search
CPC .. C07D 401/06; C07D 401/14; C07D 405/14; C07D 413/14; A61K 45/06
See application file for complete search history.

(56) References Cited

U.S. PATENT DOCUMENTS

| 10,364,255 B2 | 7/2019 | Bosanac et al. |
| 2003/0195192 A1* | 10/2003 | Haviv ............... A61K 31/551 514/218 |
| 2015/0250792 A1 | 9/2015 | Muzerelle et al. |
| 2018/0148420 A1 | 5/2018 | Casimiro-Garcia et al. |
| 2018/0354968 A1 | 12/2018 | Bosanac et al. |
| 2019/0263828 A1 | 8/2019 | Bosanac et al. |
| 2020/0069663 A1 | 3/2020 | Godbout et al. |
| 2020/0172508 A1 | 6/2020 | Fleck et al. |

FOREIGN PATENT DOCUMENTS

| WO | 2005035524 A1 | 4/2005 |
| WO | 2014048547 A1 | 4/2014 |
| WO | 2016193844 A1 | 12/2016 |
| WO | 2018011681 A1 | 1/2018 |

OTHER PUBLICATIONS

Barluenga, Jose et al. "Arylation of a-Chiral Ketones by Palladium-Catalyzed Cross-Coupling Reactions of Tosylhydrazones with Aryl Halides**" (2010) Angew. Chem. Int. Ed., 49, 6856-6859.
Berge, Stephen M. et al. "Journal of Pharmaceutical Salts" Jan. 1977, vol. 66, No. 1, 1-19.
Berruyer, C. et al. "Vanin-1 -/- Mice Exhibit a Glutathione-Mediated Tissue Resistance to Oxidative Stress" (2004) Molecular and Cellular Biology, vol. 24, No. 16, 7214-7224.
Berruyer, Carole et al. "Vanin-1 licenses inflammatory mediator production by gut epithelial cells and controls colitis by antagonizing peroxisome proliferator-activated receptor y activity" (2006) The Journal of Experimental Medicine, vol. 203, No. 13, 2817-2827.
Chai, Chi-Young et al. "VNN1 overexpression is associated with poor response to preoperative chemoradiotherapy and adverse prognosis in patients with rectal cancers" (2016) Am J Trans! Res, 8(10): 4455-4463.
Gensollen, Thomas et al. "Functional Polymorphisms in the Regulatory Regions of the VNN1 Gene are associated with Susceptibility to Inflammatory Bowel Diseases" (2013) Inflammatory Bowel Diseases, vol. 19, No. 11, 2315-2325.
International Search Report PCT/EP2018/065140 dated Jul. 31, 2018.
International Search Report PCT/EP2019/072699 dated Nov. 12, 2019.
International Search Report PCT/EP2019/083252 dated Feb. 17, 2020.

(Continued)

*Primary Examiner* — Timothy R Rozof
(74) *Attorney, Agent, or Firm* — Atabak R. Royaee

(57) ABSTRACT

The present invention encompasses compounds of the formula I

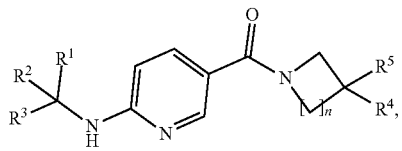

which are suitable for the treatment of diseases related to Vanin, and processes for making these compounds, pharmaceutical preparations containing these compounds, and their methods of use.

35 Claims, No Drawings

(56) References Cited

OTHER PUBLICATIONS

Jansen, Patrick a.M. et al. "Expression of the Vanin Gene Family in Normal and Inflamed Human Skin: Induction by Proinflammatory Cytokines" (2009) The Journal of Investigative Dermatology, vol. 129, No. 9, 2167-2174.

Kang, Muxing et al. "VNN1, a potential biomarker for pancreatic cancer-associated new-onset diabetes, aggravates paraneoplastic islet dysfunction by increasing oxidative stress" (2016) Cancer Letters, 373, 241-250.

Kavian, Niloufar et al. "Imbalance of the Vanin-1 Pathway in Systemic Sclerosis" (2016) The Journal of Immunology, vol. 197, 3326-3335.

Khor, Bernard et al. "Genetics and pathogenesis of inflammatory bowel disease" (2011) Nature, vol. 474, 307-317.

Lipinski, Boguslaw "Pathophysiology of oxidative stress in diabetes mellitus" (2001) Journal of Diabetes and its Complications, vol. 15, 203-210.

Martin, Florent et al. "Vanin genes are clustered (human 6q22-24 and mouse 10A2B1) and encode isoforms of pantetheinase ectoenzymes" (2001) Immunogenetics, 53: 296-306.

Martin, Florent et al. "Vanin-1 -/- mice show decreased NSAID- and Schistosoma-induced intestinal inflammation assoicated with higher glutathione stores" (2004) The Journal of Clinical Investigation, vol. 113, No. 4, 591-597.

Naquet, Philippe et al. "Role of the Vnn1 pantetheinase in tissue tolerance to stress" (2014) Biochemical Society Transactions, vol. 42, part 4, 1094-1100.

Pouyet, Laurent et al. "Epithelial vanin-1 controls inflammation-driven carcinogenesis in the colitis-associated colon cancer model" (2010) Inflammatory Bowel Diseases, vol. 16, No. 1, 96-104.

Sosa, Venus et al. "Oxidative stress and cancer: An overview" (2013) Ageing Research Reviews, vol. 12, 376-390.

Zhang, Bing et al. "The role of vanin-1 and oxidative stress-related pathways in distinguishing acute and chronic pediatric ITP" (2011) Blood, vol. 117, No. 17, 4569-4579.

* cited by examiner

HETEROAROMATIC COMPOUNDS AS VANIN INHIBITORS

BACKGROUND OF THE INVENTION

1. Technical Field

The present invention relates to novel compounds which inhibit Vanin, pharmaceutical compositions containing the same and their use as medicaments.

2. Background Information

Isoforms 1 and 2 of Vanin enzymes are single-domain extracellular pantetheinases that catalyze the cleavage of pantethine and pantetheine into pantothenic acid and cystamine and cysteamine, respectively (Martin, Immunogenetics, (2001 May-June) Vol. 53, No. 4, pp. 296-306). Generation of cysteamine has been linked to increased oxidative in tissue stress resulting from decreased glutathione levels, a condition characteristic of many pathological conditions, including IBD (Xavier, Nature. 2011 Jun. 15; 474 (7351): 307-17), cancer (Sosa, Ageing research reviews, (2013 January) Vol. 12, No. 1, pp. 376-90) and diabetes (Lipinski, Journal of diabetes and its complications, (2001 July-August) Vol. 15, No. 4, pp. 203-10).

Increased Vanin-1 activity in the gut epithelium has been implicated in promoting tissue damage and inflammation by reducing resistance to oxidative stress in murine models (Naquet, Biochem Soc Trans. 2014 August; 42(4):1094-100); (Berruyer, Molecular and cellular biology, (2004 August) Vol. 24, No. 16, pp. 7214-24); (Berruyer, The Journal of experimental medicine, (2006 Dec. 25) Vol. 203, No. 13, pp. 2817-27); (Pouyet, Inflammatory bowel diseases, (2010 January) Vol. 16, No. 1, pp. 96-104). Homozygous VNN1 knock-out (KO) mice lack appreciable levels of cysteamine in blood and tissues and show glutathione-mediated tissue resistance to oxidative stress (Berruyer, The Journal of experimental medicine, (2006 Dec. 25) Vol. 203, No. 13, pp. 2817-27). In addition, these mice are protected from intestinal injury in TNBS, DSS and *Schistosoma*-induced colitis models (Berruyer, The Journal of experimental medicine, (2006 Dec. 25) Vol. 203, No. 13, pp. 2817-27; Pouyet, Inflammatory bowel diseases, (2010 January) Vol. 16, No. 1, pp. 96-104; Martin, The Journal of clinical investigation, (2004 February) Vol. 113, No. 4, pp. 591-7). Given rodents lack Vanin-2, their only source of cysteamine is from Vanin-1, therefore the protective phenotype of the VNN1 KO mouse is attributed to the lack of cysteamine.

In humans, Vanin-1 was observed to be upregulated in intestinal epithelium in tissue biopsies from UC and CD patients and a functional polymorphism in the regulatory region of the VNN1 gene which led to increased VNN1 expression was associated with increased IBD susceptibility (P=0.0003 heterozygous vs. wild-type) (Gensollen, Inflammatory bowel diseases, (2013 October) Vol. 19, No. 11, pp. 2315-25).

In addition, upregulation of Vanin-1 activity in the skin and blood has been linked to development and severity of fibrosis in Systemic Sclerosis patients (Kavian, Journal of immunology (Baltimore, Md.: 1950), (20161015) Vol. 197, No. 8, pp. 3326-3335), and elevated levels of Vanin-1 have been observed in chronic Juvenile Idiopathic Thrombocytopenia (Zhang, Blood, (2011 Apr. 28) Vol. 117, No. 17, pp. 4569-79), Psoriasis and Atopic Dermatitis (Jansen, The Journal of investigative dermatology, (2009 September) Vol. 129, No. 9, pp. 2167-74).

Elevated Vanin-1 expression and activity are also present and serve as biomarkers for pancreatic cancer associated new-onset diabetes (Kang, Cancer Letters (New York, N.Y., United States) (2016), 373(2), 241-250) and are also correlated with poor prognosis and response to treatment in colorectal cancer (Chai, American journal of translational research, (2016) Vol. 8, No. 10, pp. 4455-4463).

WO2018011681 and WO2016193844 disclose Vanin inhibitors for the treatment of a series of diseases e.g. Crohn's disease and ulcerative colitis.

The problem to be solved by the present invention is to provide novel compounds which act as inhibitors of Vanin enzymes, preferably as inhibitors of the Vanin-1 enzyme.

It has been surprisingly found that the compounds of the present invention have potent Vanin-1 inhibitors activity, preferably exhibiting an inhibition of VNN-1 $IC_{50}$ [nM] <100, more preferred $IC_{50}$ [nM]<10, particularly preferred $IC_{50}$ [nM]<1.

Drugs with long residence times in the body are preferred because they remain effective for a longer period of time and therefore can be used in lower doses. Surprisingly the compounds of the present invention indicate favorable mean residence times (MRT).

Moreover the compounds of the present invention exhibit further capacities, which are favorable for their pharmacokinetic and pharmacological profile, e.g. good solubility and good metabolic stability. Further advantages of the compounds of the present invention are good chemical stability and good permeability.

DETAILED DESCRIPTION OF THE INVENTION

It has surprisingly been found that the problem mentioned above is solved by compounds of formula I of the present invention.

The present invention therefore relates to a compound of formula I

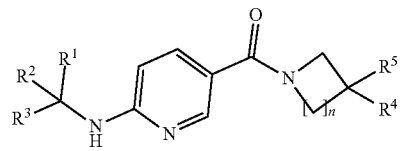

wherein n denotes 1 or 2;

$R^1$, $R^2$ and $R^3$ are independently from each other selected from the group consisting of $C_{1-4}$-alkyl optionally substituted by hydroxy, $CH_3$—O—, $CH_3$—$SO_2$—, Phenyl-$CH_2$— optionally substituted by 1 to 3 halogen atoms and 5-6 membered heteroaryl-$C_{1-2}$-alkyl-;

or $R^2$ and $R^3$ together form a 3-6 membered carbocycle or 4-6 membered heterocyclyl containing one heteroatom selected from the group consisting of N and O;

or $R^1$, $R^2$ and $R^3$ together may form or a bicyclic 5-8 membered carbocycle or a bicyclic 6-8 membered heterocyclyl containing one heteroatom selected from the group consisting of N and O;

wherein in the definition of $R^1$, $R^2$ and $R^3$ mentioned alkyl, cycloalkyl, heteroaryl and heterocyclyl are optionally substituted by 1 to 3 halogen atoms;

R⁴ denotes $R^{4.1}R^{4.2}N-$; 5-6 membered heteroaryl, NC—, 5-6 membered heterocyclyl;
or R⁴ denotes a group of formula $R^{4.a}$ or $R^{4.b}$

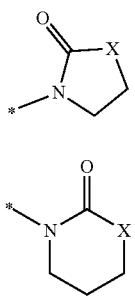

wherein
X denotes $CH_2$, $-NR^X$ or O;
  wherein $R^X$ denotes H or $C_{1-3}$-alkyl;
$R^{4.a}$ and $R^{4.b}$ independently from each other are optionally substituted by methyl;
$R^{4.1}$ is selected from the group consisting of $C_{1-4}$-alkyl-CO— optionally substituted by 1-3 F-atoms, $C_{3-4}$-cycloalkyl or $C_{1-2}$-alkoxy, $C_{3-5}$-cycloalkyl-CO— substituted with $R^{4.1.1}$ and $R^{4.1.2}$, 4-6 membered heterocyclyl-CO— substituted with $R^{4.1.3}$ and $R^{4.1.4}$, 4-6 membered heterocyclyl-$CH_2$—CO—, 5-6 membered heteroaryl-CO— optionally substituted by 1 halogen atom, $H_3C$—O— or 1 to 2 methyl, phenyl-CO— substituted with $R^{4.1.5}$ and $R^{4.1.6}$, ($C_{1-3}$-alkyl)($C_{1-3}$-alkyl)N—CO— and 5-6 membered heteroaryl;
  wherein
  $R^{4.1.1}$, $R^{4.1.2}$ independently from each other are selected from the group consisting of H, $-CH_3$, F, $CF_3$ and —CN;
  $R^{4.1.3}$, $R^{4.1.4}$ independently from each other are selected from the group consisting of H, $-CH_3$, F, $CF_3$ and —CN;
  $R^{4.1.5}$, $R^{4.1.6}$ independently from each other are selected from the group consisting of H, $-CH_3$, F, $CF_3$ and —CN;
$R^{4.2}$ is selected from the group consisting of H, $C_{1-4}$-alkyl, $C_{3-4}$-cycloalkyl, $C_{3-4}$-cycloalkyl-$C_{1-2}$-alkyl- and phenyl-$C_{1-2}$-alkyl-;
  wherein in the definition of $R^{4.2}$ mentioned alkyl, cycloalkyl and phenyl are optionally substituted by 1-3 F-atoms or one $C_{1-2}$-alkyl-O—;
$R^5$ denotes H or $C_{1-2}$-alkyl;
or
$R^4$ and $R^5$ together form 4-6 membered heterocyclyl containing 1 heteroatom selected from the group consisting of N and O;
or a pharmaceutically acceptable salt thereof.

PREFERRED EMBODIMENTS

In another embodiment of the present invention n denotes 1.

In another embodiment of the present invention n denotes 2.

In another embodiment of the present invention $R^1$ is selected from the group consisting of $C_{1-3}$-alkyl optionally substituted by hydroxy, $CH_3$—O—, $CH_3$—$SO_2$—, Phenyl-$CH_2$— optionally substituted by 1 F-atom and 5-membered heteroaryl-$C_{1-2}$-alkyl-containing 1 or 2 N-atoms.

In another embodiment of the present invention $R^1$ denotes $C_{1-3}$-alkyl optionally substituted by hydroxyl.

In another embodiment of the present invention $R^1$ denotes $C_{1-3}$-alkyl.

In another embodiment of the present invention $R^1$ denotes $CH_3$—O—.

In another embodiment of the present invention $R^1$ denotes $CH_3$—$SO_2$—.

In another embodiment of the present invention $R^1$ denotes Phenyl-$CH_2$— optionally substituted by 1 F-atom.

In another embodiment of the present invention $R^1$ denotes 5-membered heteroaryl-$C_{1-2}$-alkyl-containing 1 or 2 N-atoms.

In another embodiment of the present invention $R^1$ denotes methyl.

In another embodiment of the present invention $R^1$ denotes ethyl.

In another embodiment of the present invention $R^1$ denotes propyl.

In another embodiment of the present invention $R^2$ is selected from the group consisting of $C_{1-3}$-alkyl optionally substituted by hydroxy, $CH_3$—O—, $CH_3$—$SO_2$—, Phenyl-$CH_2$— optionally substituted by 1 F-atom and 5-membered heteroaryl-$C_{1-2}$-alkyl-containing 1 or 2 N-atoms.

In another embodiment of the present invention $R^2$ denotes $C_{1-3}$-alkyl optionally substituted by hydroxyl.

In another embodiment of the present invention $R^2$ denotes $C_{1-3}$-alkyl.

In another embodiment of the present invention $R^2$ denotes $CH_3$—O—.

In another embodiment of the present invention $R^2$ denotes $CH_3$—$SO_2$—.

In another embodiment of the present invention $R^2$ denotes Phenyl-$CH_2$— optionally substituted by 1 F-atom.

In another embodiment of the present invention $R^2$ denotes 5-membered heteroaryl-$C_{1-2}$-alkyl-containing 1 or 2 N-atoms.

In another embodiment of the present invention $R^2$ denotes methyl.

In another embodiment of the present invention $R^2$ denotes ethyl.

In another embodiment of the present invention $R^2$ denotes propyl.

In another embodiment of the present invention $R^3$ is selected from the group consisting of $C_{1-3}$-alkyl optionally substituted by hydroxy, $CH_3$—O—, $CH_3$—$SO_2$—, Phenyl-$CH_2$— optionally substituted by 1 F-atom and 5-membered heteroaryl-$C_{1-2}$-alkyl-containing 1 or 2 N-atoms.

In another embodiment of the present invention $R^3$ denotes $C_{1-3}$-alkyl optionally substituted by hydroxyl.

In another embodiment of the present invention $R^3$ denotes methyl.

In another embodiment of the present invention $R^3$ denotes ethyl.

In another embodiment of the present invention $R^3$ denotes propyl.

In another embodiment of the present invention $R^3$ denotes $CH_3$—O—.

In another embodiment of the present invention $R^3$ denotes $CH_3$—$SO_2$—.

In another embodiment of the present invention $R^3$ denotes Phenyl-$CH_2$— optionally substituted by 1 F-atom.

In another embodiment of the present invention $R^3$ denotes 5-membered heteroaryl-$C_{1-2}$-alkyl-containing 1 or 2 N-atoms.

In another embodiment of the present invention $R^3$ denotes $C_{1-3}$-alkyl optionally substituted by hydroxyl.

In another embodiment of the present invention $R^1$, $R^2$ and $R^3$ denote methyl.

In another embodiment of the present invention $R^1$ and $R^2$ denote methyl.

In another embodiment of the present invention
$R^1$, $R^2$ and $R^3$ together may form or a bicyclic 5-6 membered carbocycle or a bicyclic 6-8 membered heterocyclyl containing one heteroatom selected from the group consisting of N and O;
wherein in the definition of $R^1$, $R^2$ and $R^3$ mentioned alkyl, cycloalkyl, heteroaryl and
heterocyclyl are optionally substituted by 1 to 3 F or Cl atoms, preferably F atoms;

In another embodiment of the present invention
$R^1$, $R^2$ and $R^3$ together may form or a bicyclic 5 membered carbocycle.

In another embodiment of the present invention
$R^2$ and $R^3$ together form a 4-6 membered carbocycle or 6-membered heterocyclyl containing one oxygen atom.

In another embodiment of the present invention $R^2$ and $R^3$ together form a 4-6 membered carbocycle.

In another embodiment of the present invention $R^2$ and $R^3$ together form cyclobutyl.

In another embodiment of the present invention $R^2$ and $R^3$ together form cyclopentyl.

In another embodiment of the present invention $R^2$ and $R^3$ together form cyclohexyl.

In another embodiment of the present invention $R^2$ and $R^3$ together form a 6-membered heterocyclyl containing one oxygen atom.

In another embodiment of the present invention
$R^4$ is selected from the group consisting of $R^{4.1}R^{4.2}N$—, pyridinyl and NC—;
or $R^4$ denotes a group of formula $R^{4.a}$ or $R^{4.b}$

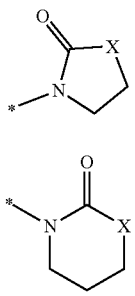

X denotes $CH_2$ or O;
$R^{4.a}$ and $R^{4.b}$ independently from each other are optionally substituted by methyl,
$R^{4.1}$ is selected from the group consisting of $C_{1-2}$-alkyl-CO—, $C_{3-4}$-cycloalkyl-CO— substituted with $R^{4.1.1}$ and $R^{4.1.2}$, 5-6 membered heterocyclyl-CO— substituted with $R^{4.1.3}$ and $R^{4.1.4}$, 6 membered heterocyclyl-$CH_2$—CO—, 5 membered heteroaryl-CO— optionally substituted by 1-3 halogen atoms, phenyl-CO— substituted with $R^{4.1.5}$ and $R^{4.1.6}$, 6 membered heteroaryl;
wherein
$R^{4.1.1}$, $R^{4.1.2}$ independently from each other are selected from the group consisting of H, —$CH_3$, F, $CF_3$ and —CN;

$R^{4.1.3}$, $R^{4.1.4}$ independently from each other are selected from the group consisting of H, —$CH_3$, F, $CF_3$ and —CN;
$R^{4.1.5}$, $R^{4.1.6}$ independently from each other are selected from the group consisting of H, —$CH_3$, F, $CF_3$ and —CN;
$R^{4.2}$ denotes methyl.

In another embodiment of the present invention
$R^4$ denotes a group of formula $R^{4.a}$ or $R^{4.b}$

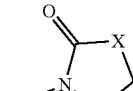

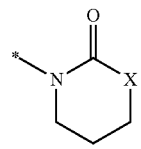

wherein
X denotes $CH_2$ or O;
$R^{4.a}$ and $R^{4.b}$ independently from each other are optionally substituted by methyl, In another embodiment of the present invention $R^4$ denotes a group of formula $R^{4.a}$, wherein
X denotes $CH_2$ or O;
$R^{4.a}$ is optionally substituted by methyl.

In another embodiment of the present invention $R^4$ denotes a group of formula
$R^{4.b}$, wherein
X denotes $CH_2$ or O;
$R^{4.b}$ is optionally substituted by methyl.

In another embodiment of the present invention X denotes $CH_2$.

In another embodiment of the present invention X denotes O.

In another embodiment of the present invention $R^4$ is selected from the group consisting of $R^{4.1}R^{4.2}N$—, pyridinyl, pyrimidinyl and NC—.

In another embodiment of the present invention $R^4$ denotes $R^{4.1}R^{4.2}N$—.

In another embodiment of the present invention $R^4$ denotes pyridinyl.

In another embodiment of the present invention $R^4$ denotes pyrimidinyl.

In another embodiment of the present invention $R^4$ denotes NC—.

In another embodiment of the present invention $R^{4.1}$ is selected from the group consisting of $C_{1-2}$-alkyl-CO—, $C_{3-4}$-cycloalkyl-CO— optionally substituted with F or CN, 5-6 membered heterocyclyl-CO— optionally substituted with methyl or $CF_3$, morpholinyl-$CH_2$—CO—, thiophen optionally substituted with Cl and phenyl-CO— optionally substituted with one F-atom, pyrimidine.

In another embodiment of the present invention $R^{4.1}$ denotes $C_{1-2}$-alkyl-CO—.

In another embodiment of the present invention $R^{4.1}$ denotes methyl-CO—.

In another embodiment of the present invention $R^{4.1}$ denotes $C_{3-4}$-cycloalkyl-CO— substituted with $R^{4.1.1}$ and $R^{4.1.2}$.

In another embodiment of the present invention $R^{4.1}$ denotes 5-6 membered heterocyclyl-CO— substituted with $R^{4.1.3}$ and $R^{4.1.4}$.

In another embodiment of the present invention $R^{4.1}$ denotes 6 membered heterocyclyl-CH$_2$—CO—.

In another embodiment of the present invention $R^{4.1}$ denotes 5 membered heteroaryl-CO— optionally substituted by 1-3 halogen atoms.

In another embodiment of the present invention $R^{4.1}$ denotes phenyl-CO— substituted with $R^{4.1.5}$ and $R^{4.1.6}$.

In another embodiment of the present invention $R^{4.1}$ denotes 6 membered heteroaryl, preferably pyrimidine.

In another embodiment of the present invention $R^{4.1.1}$ and $R^{4.1.2}$ denote H.

In another embodiment of the present invention $R^{4.1.1}$ and $R^{4.1.2}$ denote F.

In another embodiment of the present invention $R^{4.1.1}$ denotes H and $R^{4.1.2}$ denotes F.

In another embodiment of the present invention $R^{4.1.1}$ denotes H and $R^{4.1.2}$ denotes —CN.

In another embodiment of the present invention $R^{4.1.3}$ and $R^{4.1.4}$ denote H.

In another embodiment of the present invention $R^{4.1.3}$ denotes H and $R^{4.1.4}$ denotes CH$_3$.

In another embodiment of the present invention $R^{4.1.3}$ denotes H and $R^{4.1.4}$ denotes CF$_3$.

In another embodiment of the present invention $R^{4.1.3}$ denotes CH$_3$ and $R^{4.1.4}$ denotes CF$_3$.

In another embodiment of the present invention $R^{4.1.5}$ and $R^{4.1.6}$ denote H.

In another embodiment of the present invention $R^{4.1.5}$ denotes H and $R^{4.1.6}$ denotes F.

In another embodiment of the present invention $R^{4.1.5}$ and $R^{4.1.6}$ denote F.

In another embodiment of the present invention $R^{4.2}$ denotes methyl optionally substituted by 1-3 F-atoms or one $C_{1-2}$-alkyl-O—.

In another embodiment of the present invention $R^{4.2}$ denotes methyl.

In another embodiment of the present invention $R^5$ denotes H or methyl.

In another embodiment of the present invention $R^5$ denotes H.

In another embodiment of the present invention $R^5$ denotes methyl.

In another embodiment of the present invention
n denotes 1 or 2,
$R^1$ denotes methyl,
$R^2$ denotes methyl,
$R^3$ denotes $C_{1-3}$-alkyl optionally substituted by hydroxyl, or
$R^2$ and $R^3$ together form a 4-6 membered carbocycle or a 6-membered heterocyclyl containing one oxygen atom,
$R^4$ is selected from the group consisting of $R^{4.1}R^{4.2}N$—, pyridinyl and NC—
or
$R^4$ denotes a group of formula $R^{4.a}$ or $R^{4.b}$

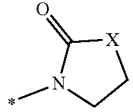

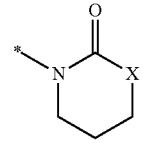

wherein
X denotes CH$_2$ or O;
$R^{4.a}$ and $R^{4.b}$ independently from each other are optionally substituted by methyl,
$R^{4.1}$ is selected from the group consisting of $C_{1-4}$-alkyl-CO—, $C_{3-5}$-cycloalkyl-CO— substituted with $R^{4.1.1}$ and $R^{4.1.2}$, 4-6 membered heterocyclyl-CO— substituted with $R^{4.1.3}$ and $R^{4.1.4}$, 6 membered heterocyclyl-CH$_2$—CO—, 5-6 membered heteroaryl-CO— optionally substituted by 1-3 halogen atoms, phenyl-CO— substituted with $R^{4.1.5}$ and $R^{4.1.6}$ and 6 membered heteroaryl containing 1 or 2 N-atoms.
wherein
$R^{4.1.1}$, $R^{4.1.2}$ independently from each other are selected from the group consisting of H, F and —CN;
$R^{4.1.3}$, $R^{4.1.4}$ independently from each other are selected from the group consisting of H, —CH$_3$ and CF$_3$;
$R^{4.1.5}$, $R^{4.1.6}$ independently from each other are selected from the group consisting of H and F;
$R^{4.2}$ denotes methyl;
$R^5$ denotes H or methyl.
A compound according to claim 1, wherein
n denotes 2,
$R^1$ denotes methyl,
$R^2$ denotes methyl
$R^3$ denotes $C_{1-3}$-alkyl optionally substituted by hydroxyl,
$R^4$ is selected from the group consisting of $R^{4.1}R^{4.2}N$—, pyridinyl and NC—
or
$R^4$ denotes a group of formula $R^{4.a}$ or $R^{4.b}$

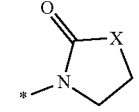

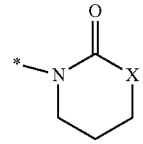

wherein
X denotes CH$_2$ or O;
$R^{4.a}$ and $R^{4.b}$ independently from each other are optionally substituted by methyl,
$R^{4.1}$ is selected from the group consisting of $C_{1-4}$-alkyl-CO—, $C_{3-5}$-cycloalkyl-CO— substituted with $R^{4.1.1}$ and $R^{4.1.2}$, 4-6 membered heterocyclyl-CO— substituted with $R^{4.1.3}$ and $R^{4.1.4}$, 6 membered heterocyclyl-CH$_2$—CO—, 5-6 membered heteroaryl-CO— optionally substituted by 1-3 halogen atoms, phenyl-CO— substituted with $R^{4.1.5}$ and $R^{4.1.6}$ and 6 membered heteroaryl containing 1 or 2 N-atoms.
wherein
$R^{4.1.1}$, $R^{4.1.2}$ independently from each other are selected from the group consisting of H, F and —CN;
$R^{4.1.3}$, $R^{4.1.4}$ independently from each other are selected from the group consisting of H, —CH$_3$ and CF$_3$;
$R^{4.1.5}$, $R^{4.1.6}$ independently from each other are selected from the group consisting of H and F;
$R^{4.2}$ denotes methyl;
$R^5$ denotes H or methyl;
or a pharmaceutically acceptable salt thereof.
A compound according to claim 1, wherein
n denotes 2,
$R^1$ denotes methyl,
$R^2$ and $R^3$ together form a 4-6 membered carbocycle or a 6-membered heterocyclyl containing one oxygen atom,
$R^4$ is selected from the group consisting of $R^{4.1}R^{4.2}N$—, pyridinyl and NC—
or
$R^4$ denotes a group of formula $R^{4.a}$ or $R^{4.b}$

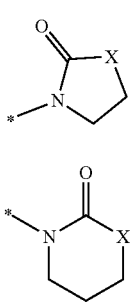

wherein
X denotes CH$_2$ or O;
$R^{4.a}$ and $R^{4.b}$ independently from each other are optionally substituted by methyl,
$R^{4.1}$ is selected from the group consisting of $C_{1-4}$-alkyl-CO—, $C_{3-5}$-cycloalkyl-CO— substituted with $R^{4.1.1}$ and $R^{4.1.2}$, 4-6 membered heterocyclyl-CO— substituted with $R^{4.1.3}$ and $R^{4.1.4}$, 6 membered heterocyclyl-CH$_2$—CO—, 5-6 membered heteroaryl-CO— optionally substituted by 1-3 halogen atoms, phenyl-CO— substituted with $R^{4.1.5}$ and $R^{4.1.6}$ and 6 membered heteroaryl containing 1 or 2 N-atoms.
wherein
$R^{4.1.1}$, $R^{4.1.2}$ independently from each other are selected from the group consisting of H, F and —CN;
$R^{4.1.3}$, $R^{4.1.4}$ independently from each other are selected from the group consisting of H, —CH$_3$ and CF$_3$;
$R^{4.1.5}$, $R^{4.1.6}$ independently from each other are selected from the group consisting of H and F;
$R^{4.2}$ denotes methyl;
$R^5$ denotes H or methyl;
or a pharmaceutically acceptable salt thereof.
A compound according to claim 1, wherein
n denotes 2,
$R^1$ denotes methyl,
$R^2$ denotes methyl $R^3$ denotes $C_{1-3}$-alkyl optionally substituted by hydroxyl,
$R^4$ denotes $R^{4.1}R^{4.2}N$,
$R^{4.1}$ is selected from the group consisting of $C_{1-4}$-alkyl-CO—, $C_{3-5}$-cycloalkyl-CO— substituted with $R^{4.1.1}$ and $R^{4.1.2}$, 4-6 membered heterocyclyl-CO— substituted with $R^{4.1.3}$ and $R^{4.1.4}$, 6 membered heterocyclyl-CH$_2$—CO—, 5-6 membered heteroaryl-CO— optionally substituted by 1-3 halogen atoms, phenyl-CO— substituted with $R^{4.1.5}$ and $R^{4.1.6}$ and 6 membered heteroaryl containing 1 or 2 N-atoms.
wherein
$R^{4.1.1}$, $R^{4.1.2}$ independently from each other are selected from the group consisting of H, F and —CN;
$R^{4.1.3}$, $R^{4.1.4}$ independently from each other are selected from the group consisting of H, —CH$_3$ and CF$_3$;
$R^{4.1.5}$, $R^{4.1.6}$ independently from each other are selected from the group consisting of H and F;
$R^{4.2}$ denotes methyl;
$R^5$ denotes H or methyl;
or a pharmaceutically acceptable salt thereof.
A further preferred embodiment of the present invention are the above compounds of formula I, selected from the group consisting of examples 1.2, 1.3, 1.5, 1.6, 1.8, 1.9, 1.11, 3.2, 5.1 and 7.1.

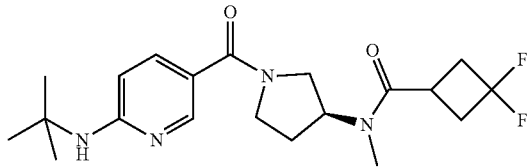

Ex. 1.2

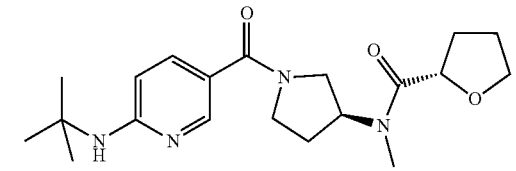

Ex. 1.3

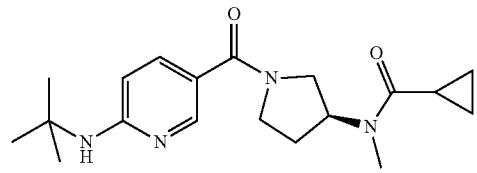

Ex. 1.5

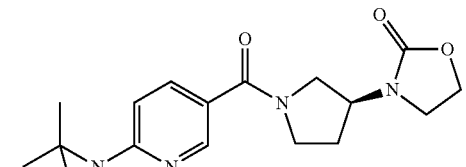

Ex. 1.6

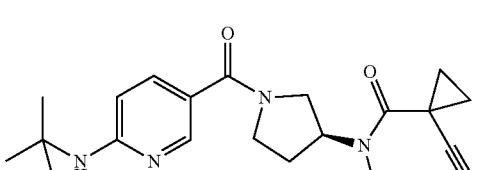

Ex. 1.8

-continued

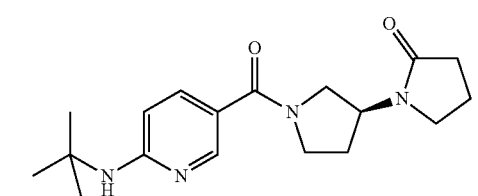
Ex. 1.9

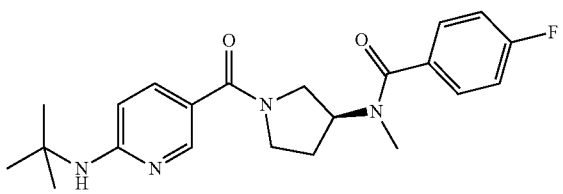
Ex. 1.11

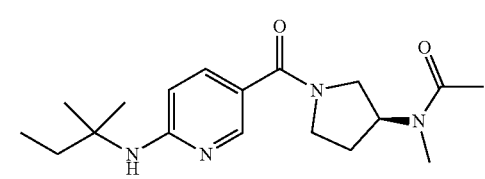
Ex. 3.2

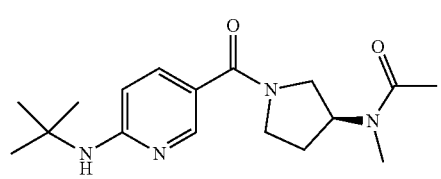
Ex. 5.1

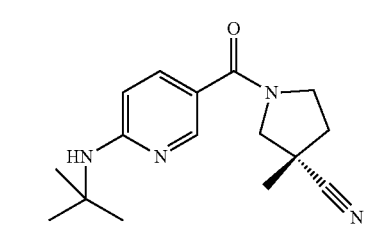
Ex. 7.1 or a pharmaceutically acceptable salt thereof.

A further preferred embodiment of the current invention are the above compounds of formula I, selected from the group consisting of examples 1.2, 1.3, 1.5, 1.6, 1.8, 1.9, 1.11, 5.1 and 7.1.

A further preferred embodiment of the current invention are the above compounds of formula I, selected from the group consisting of examples 1.2, 1.3, 1.5, 1.8, 1.11, 3.2 and 5.1.

A further preferred embodiment of the current invention are the above compounds of formula I, selected from the group consisting of examples 1.6 and 1.9.

A further preferred embodiment of the current invention is the compound of example 1.2.

A further preferred embodiment of the current invention is the compound of example 1.3

A further preferred embodiment of the current invention is the compound of example 1.5.

A further preferred embodiment of the current invention is the compound of example 1.6.

A further preferred embodiment of the current invention is the compound of example 1.8.

A further preferred embodiment of the current invention is the compound of example 1.9.

A further preferred embodiment of the current invention is the compound of example 1.11.

A further preferred embodiment of the current invention is the compound of example 3.2.

A further preferred embodiment of the current invention is the compound of example 5.1.

A further preferred embodiment of the current invention is the compound of example 7.1.

A further preferred embodiment of the current invention are pharmaceutically acceptable salts of the above compounds of formula I, selected from the group consisting of examples 1.2, 1.3, 1.5, 1.6, 1.8, 1.9, 1.11, 5.1 and 7.1.

A further preferred embodiment of the current invention are pharmaceutically acceptable salts of the above compounds of formula I, selected from the group consisting of examples 1.2, 1.3, 1.5, 1.8, 1.11, 3.2 and 5.1.

A further preferred embodiment of the current invention are pharmaceutically acceptable salts of the above compounds of formula I, selected from the group consisting of examples 1.6 and 1.9.

A further preferred embodiment of the current invention are pharmaceutically acceptable salts of the compound of example 1.2.

A further preferred embodiment of the current invention are pharmaceutically acceptable salts of the compound of example 1.3

A further preferred embodiment of the current invention are pharmaceutically acceptable salts of the compound of example 1.5.

A further preferred embodiment of the current invention are pharmaceutically acceptable salts of the compound of example 1.6.

A further preferred embodiment of the current invention are pharmaceutically acceptable salts of the compound of example 1.8.

A further preferred embodiment of the current invention are pharmaceutically acceptable salts of the compound of example 1.9.

A further preferred embodiment of the current invention are pharmaceutically acceptable salts of the compound of example 1.11.

A further preferred embodiment of the current invention are pharmaceutically acceptable salts of the compound of example 3.2.

A further preferred embodiment of the current invention are pharmaceutically acceptable salts of the compound of example 5.1.

A further preferred embodiment of the current invention are pharmaceutically acceptable salts of the compound of example 7.1.

Another embodiment of the present invention are compounds of formula IA or the pharmaceutically acceptable salts thereof.

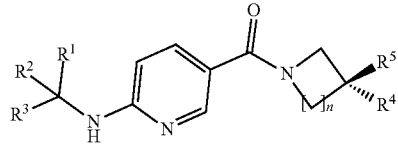
IA

Another embodiment of the present invention are compounds of formula IB or the pharmaceutically acceptable salts thereof.

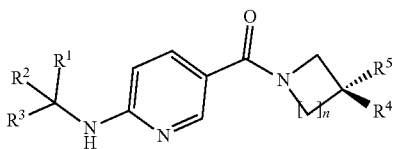

Any and each of the definitions of $R^1$, $R^2$, $R^3$, $R^4$, $R^5$, $R^{4.1}$, $R^{4.2}$, $R^{4.1.1}$, $R^{4.1.2}$, $R^{4.1.3}$, $R^{4.1.4}$, $R^{4.1.5}$, $R^{4.1.6}$, $R^x$, n and X may be combined with each other.

A further embodiment of the current invention is a pharmaceutical composition comprising a therapeutically effective amount of at least one compound of formula I or a pharmaceutically acceptable salt thereof and one or more pharmaceutically acceptable excipients.

A further embodiment of the current invention is a compound of formula I or a pharmaceutically acceptable salt thereof for use as a medicament Furthermore, the present invention relates to the use of a compound of general formula I for the treatment and/or prevention of a disease and/or condition associated with or modulated by Vanin-1 or Vanin-2, especially Vanin-1, including but not limited to the treatment and/or prevention of inflammatory diseases, preferably inflammatory bowel diseases.

A further embodiment of the current invention is the use of a compound of formula I for treating a patient suffering from Crohn's disease, ulcerative colitis, atopic dermatitis, systemic sclerosis, Non-Alcoholic Steatohepathitis (NASH), psoriasis, chronic kidney disease, chronic obstructive pulmonary disease, idiopathic pulmonary fibrosis, rheumatoid arthritis, scleroderma, asthma, allergic rhinitis, allergic eczema, juvenile rheumatoid arthritis, juvenile idiopathic arthritis, graft versus host disease, psoriatic arthritis, Hyperlipidemia, colorectal cancer or pancreatic cancer related new onset diabetes.

A further embodiment of the current invention is the use of a compound of formula I for treating a patient suffering from Crohn's disease, ulcerative colitis, systemic sclerosis, Non-Alcoholic Steatohepathitis (NASH), chronic obstructive pulmonary disease or atopic dermatitis, preferably Crohn's disease, ulcerative colitis, systemic sclerosis, Non-Alcoholic Steatohepathitis (NASH) or atopic dermatitis, particularly preferred from Crohn's disease or ulcerative colitis.

A further embodiment of the current invention is the use of a compound of formula I for treating a patient suffering from moderate to severe Crohn's disease.

A further embodiment of the current invention is the use of a compound of formula I for treating a patient suffering from ulcerative colitis.

A further embodiment of the current invention is the use of a compound of formula I for treating a patient suffering from atopic dermatitis.

A further embodiment of the current invention is the use of a compound of formula I for treating a patient suffering from NASH.

In a further embodiment, there is provided a method of treating a disease chosen from Crohn's disease, ulcerative colitis, atopic dermatitis, systemic sclerosis, Non-Alcoholic Steatohepathitis (NASH), psoriasis, chronic kidney disease, chronic obstructive pulmonary disease, idiopathic pulmonary fibrosis, rheumatoid arthritis, scleroderma, asthma, allergic rhinitis, allergic eczema, juvenile rheumatoid arthritis, juvenile idiopathic arthritis, graft versus host disease, psoriatic arthritis, Hyperlipidemia, colorectal cancer or pancreatic cancer related new onset diabetes comprising administering to a patient a therapeutically effective amount of a compound according to the first embodiment or any of its related embodiments or a pharmaceutically acceptable salt thereof.

In a further embodiment, there is provided a process for preparation of a compound according to the first embodiment or any of its related embodiments by the methods shown herein below.

In a further aspect the present invention relates to a compound of general formula 1 for use in the treatment and/or prevention of above mentioned diseases and conditions.

In a further aspect the present invention relates to the use of a compound of general formula 1 for the preparation of a medicament for the treatment and/or prevention of above mentioned diseases and conditions.

In a further aspect the present invention relates to methods for the treatment or prevention of above mentioned diseases and conditions, which method comprises the administration of an effective amount of a compound of general formula 1 to a human being.

The actual pharmaceutically effective amount or therapeutic dosage will usually depend on factors known by those skilled in the art such as age and weight of the patient, route of administration and severity of disease. In any case the compounds will be administered at dosages and in a manner which allows a pharmaceutically effective amount to be delivered based upon patient's unique condition.

A further embodiment of the current invention is a pharmaceutical composition comprising additionally to a compound of formula I, a pharmaceutically active compound selected from the group consisting of an immunomodulatory agent, anti-inflammatory agent or a chemotherapeutic agent.

A further embodiment of the current invention is a pharmaceutical composition comprising additionally to a compound of formula I, a pharmaceutically active compound selected from the group consisting of an immunomodulatory agent, anti-inflammatory agent, or a chemotherapeutic agent. Examples of such agents include but are not limited to cyclophosphamide, mycophenolate (MMF), hydroxychloroquine, glucocorticoids, corticosteroids, immunosuppressants, NSAIDs, non-specific and COX-2 specific cyclooxygenase enzyme inhibitors, tumour necrosis factor receptor (TNF) receptors antagonists, IL12/23 and IL23 antagonists, 4037 integrin blocking antibodies, non-selective and selective JAK kinase inhibitors and methotrexate, but also combinations of two or three active substances.

Definitions

Terms not specifically defined herein should be given the meanings that would be given to them by one of skill in the art in light of the disclosure and the context. As used in the specification, however, unless specified to the contrary, the following terms have the meaning indicated and the following conventions are adhered to.

In the groups, radicals, or moieties defined below, the number of carbon atoms is often specified preceding the group, for example, $C_{1-6}$-alkyl means an alkyl group or radical having 1 to 6 carbon atoms. In general in groups like HO, $H_2N$, (O)S, $(O)_2S$, CN (cyano), HOOC, $F_3C$ or the like, the skilled artisan can see the radical attachment point(s) to the molecule from the free valences of the group itself. For combined groups comprising two or more subgroups, the last named subgroup is the radical attachment point, for example, the substituent "aryl-$C_{1-3}$-alkyl" means an aryl group which is bound to a $C_{1-3}$-alkyl-group, the latter of which is bound to the core or to the group to which the substituent is attached.

In case a compound of the present invention is depicted in form of a chemical name and as a formula in case of any discrepancy the formula shall prevail.

The numeration of the atoms of a substituent starts with the atom which is closest to the core or to the group to which the substituent is attached.

For example, the term "3-carboxypropyl-group" represents the following substituent:

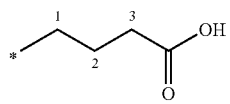

wherein the carboxy group is attached to the third carbon atom of the propyl group. The terms "1-methylpropyl-", "2,2-dimethylpropyl-" or "cyclopropylmethyl-" group represent the following groups:

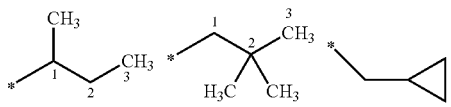

The asterisk may be used in sub-formulas to indicate the bond which is connected to the core molecule as defined.

The term "substituted" as used herein, means that any one or more hydrogens on the designated atom is replaced with a selection from the indicated group, provided that the designated atom's normal valence is not exceeded, and that the substitution results in a stable compound.

Unless specifically indicated, throughout the specification and the appended claims, a given chemical formula or name shall encompass tautomers and all stereo, optical and geometrical isomers (e.g. enantiomers, diastereomers, E/Z isomers etc. . . . ) and racemates thereof as well as mixtures in different proportions of the separate enantiomers, mixtures of diastereomers, or mixtures of any of the foregoing forms where such isomers and enantiomers exist, as well as salts, including pharmaceutically acceptable salts thereof and solvates thereof such as for instance hydrates including solvates of the free compounds or solvates of a salt of the compound.

In general, substantially pure stereoisomers can be obtained according to synthetic principles known to a person skilled in the field, e.g. by separation of corresponding mixtures, by using stereochemically pure starting materials and/or by stereoselective synthesis. It is known in the art how to prepare optically active forms, such as by resolution of racemic forms or by synthesis, e.g. starting from optically active starting materials and/or by using chiral reagents.

Enantiomerically pure compounds of this invention or intermediates may be prepared via asymmetric synthesis, for example by preparation and subsequent separation of appropriate diastereomeric compounds or intermediates which can be separated by known methods (e.g. by chromatographic separation or crystallization) and/or by using chiral reagents, such as chiral starting materials, chiral catalysts or chiral auxiliaries.

Further, it is known to the person skilled in the art how to prepare enantiomerically pure compounds from the corresponding racemic mixtures, such as by chromatographic separation of the corresponding racemic mixtures on chiral stationary phases; or by resolution of a racemic mixture using an appropriate resolving agent, e.g. by means of diastereomeric salt formation of the racemic compound with optically active acids or bases, subsequent resolution of the salts and release of the desired compound from the salt; or by derivatization of the corresponding racemic compounds with optically active chiral auxiliary reagents, subsequent diastereomer separation and removal of the chiral auxiliary group; or by kinetic resolution of a racemate (e.g. by enzymatic resolution); by enantioselective crystallization from a conglomerate of enantiomorphous crystals under suitable conditions; or by (fractional) crystallization from a suitable solvent in the presence of an optically active chiral auxiliary.

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, and commensurate with a reasonable benefit/risk ratio.

As used herein, "pharmaceutically acceptable salt" refer to derivatives of the disclosed compounds wherein the parent compound is modified by making acid or base salts thereof.

Examples of pharmaceutically acceptable salts include, but are not limited to, mineral or organic acid salts of basic residues such as amines; alkali or organic salts of acidic residues such as carboxylic acids; and the like.

For example, such salts include salts from benzenesulfonic acid, benzoic acid, citric acid, ethanesulfonic acid, fumaric acid, gentisic acid, hydrobromic acid, hydrochloric acid, maleic acid, malic acid, malonic acid, mandelic acid, methanesulfonic acid, 4-methyl-benzenesulfonic acid, phosphoric acid, salicylic acid, succinic acid, sulfuric acid and tartaric acid.

Further pharmaceutically acceptable salts can be formed with cations from ammonia, L-arginine, calcium, 2,2'-iminobisethanol, L-lysine, magnesium, N-methyl-D-glucamine, potassium, sodium and tris(hydroxymethyl)-aminomethane.

The pharmaceutically acceptable salts of the present invention can be synthesized from the parent compound which contains a basic or acidic moiety by conventional chemical methods.

Generally, such salts can be prepared by reacting the free acid or base forms of these compounds with a sufficient amount of the appropriate base or acid in water or in an organic diluent like ether, ethyl acetate, ethanol, isopropanol, or acetonitrile, or a mixture thereof.

Salts of other acids than those mentioned above which for example are useful for purifying or isolating the compounds of the present invention (e.g. trifluoro acetate salts,) also comprise a part of the invention.

The term halogen generally denotes fluorine, chlorine, bromine and iodine.

The term "$C_{1-n}$-alkyl", wherein n is an integer selected from 2, 3, 4, 5 or 6, preferably 4 or 6, either alone or in combination with another radical denotes an acyclic, saturated, branched or linear hydrocarbon radical with 1 to n C atoms. For example the term $C_{1-5}$-alkyl embraces the radicals $H_3C-$, $H_3C-CH_2-$, $H_3C-CH_2-CH_2-$, $H_3C-CH(CH_3)-$, $H_3C-CH_2-CH_2-CH_2-$, $H_3C-CH(CH_3)-CH_2-$, $H_3C-CH(CH_3)-CH_2-$, $H_3C-C(CH_3)_2-$, $H_3C-CH_2-CH_2-CH_2-CH_2-$, $H_3C-CH_2-CH_2-$ CH(CH₃)—, H₃C—CH₂—CH(CH₃)—CH₂—, H₃C—CH(CH₃)—CH₂—CH₂—, H₃C—CH₂—C(CH₃)₂—, H₃C—C(CH₃)₂—CH₂—, H₃C—CH(CH₃)—CH(CH₃)— and H₃C—CH₂—CH(CH₂CH₃)—.

The term "C$_{3-n}$-cycloalkyl", wherein n is an integer from 4 to n, either alone or in combination with another radical denotes a cyclic, saturated, unbranched hydrocarbon radical with 3 to n C atoms. For example the term C$_{3-7}$-cycloalkyl includes cyclopropyl, cyclobutyl, cyclopentyl, cyclohexyl and cycloheptyl.

The term "carbocyclyl" or "carbocycle" as used either alone or in combination with another radical, means a mono-bi- or tricyclic ring structure consisting of 3 to 14 carbon atoms. The term "carbocyclyl" or "carbocycle" refers to fully saturated and aromatic ring systems and partially saturated ring systems. The term "carbocyclyl" or "carbocycle" encompasses fused, bridged and spirocyclic systems.

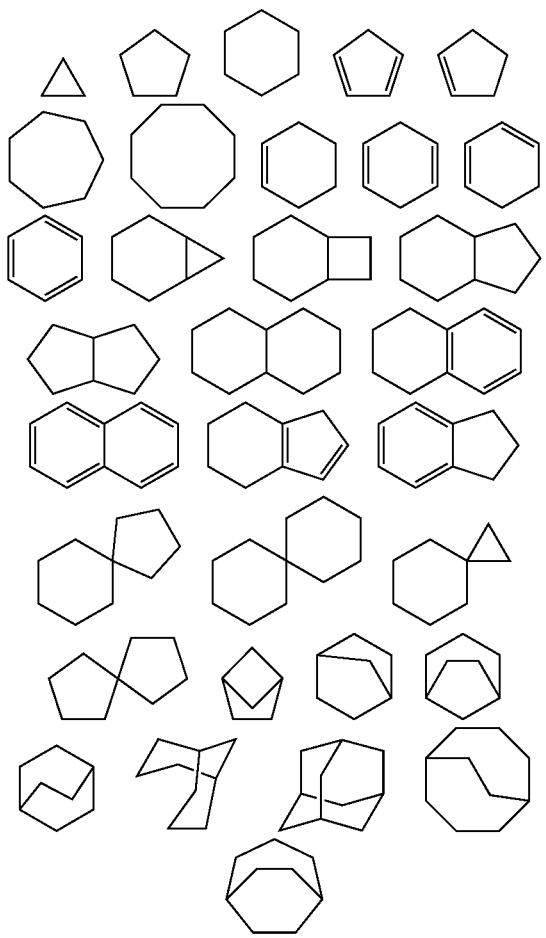

The term "aryl" as used herein, either alone or in combination with another radical, denotes a carbocyclic aromatic monocyclic group containing 6 carbon atoms which is optionally further fused to a second five- or six-membered, carbocyclic group which is optionally aromatic, saturated or unsaturated. Aryl includes, but is not limited to, phenyl, indanyl, indenyl, naphthyl, anthracenyl, phenanthrenyl, tetrahydronaphthyl and dihydronaphthyl.

The term "heterocyclyl" or "heterocycle" means a saturated or unsaturated mono- or polycyclic-ring systems including aromatic ring system containing one or more heteroatoms selected from N, O or S(O)$_r$, wherein r=0, 1 or 2, consisting of 3 to 14 ring atoms wherein none of the heteroatoms is part of the aromatic ring. The term "heterocyclyl" or "heterocycle" is intended to include all the possible isomeric forms.

Thus, the term "heterocyclyl" or "heterocycle" includes the following exemplary structures which are not depicted as radicals as each form are optionally attached through a covalent bond to any atom so long as appropriate valences are maintained:

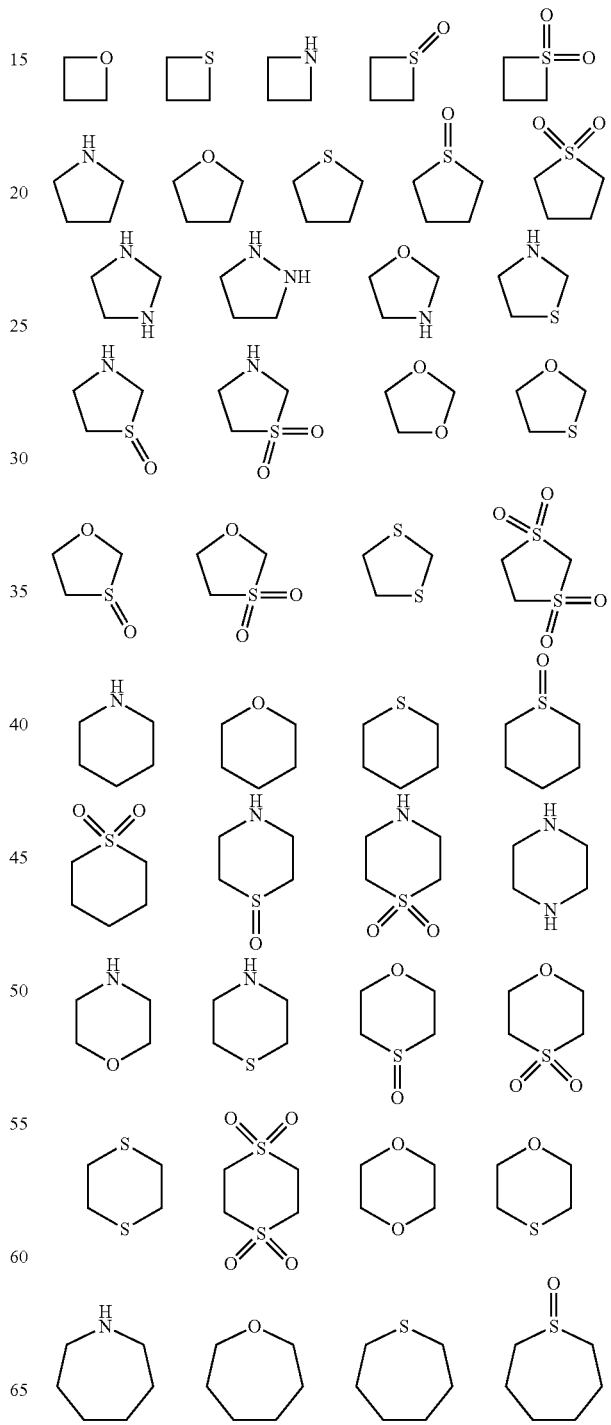

-continued
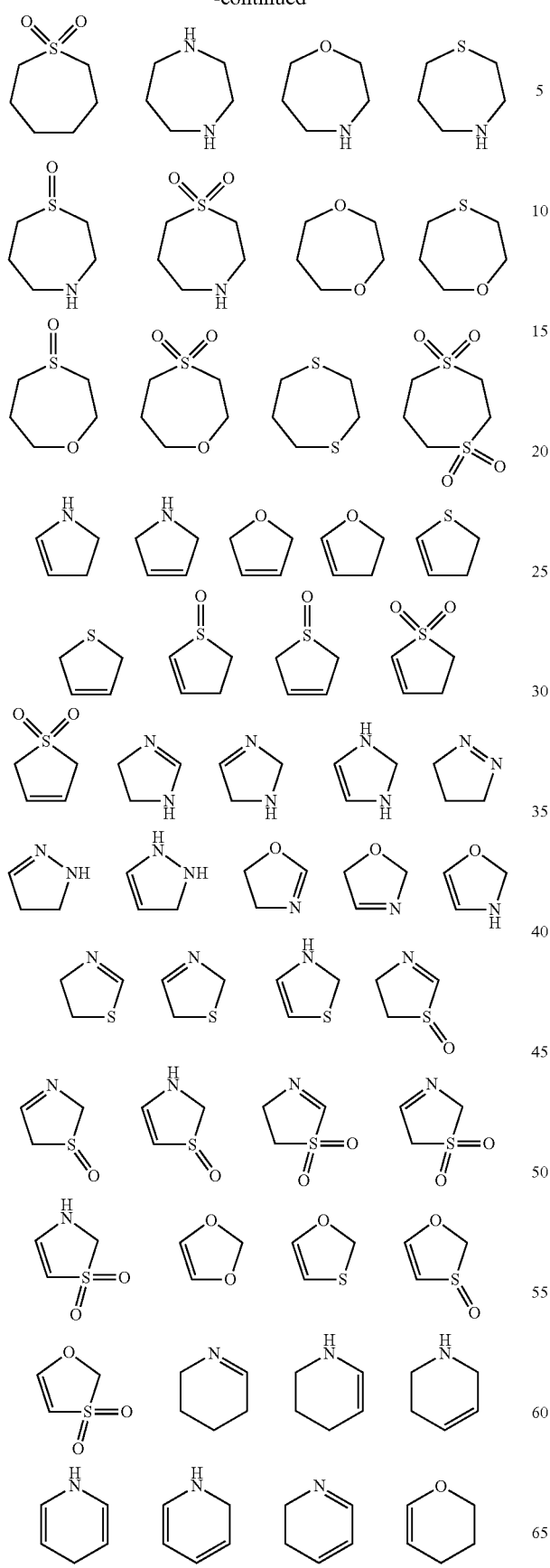
-continued
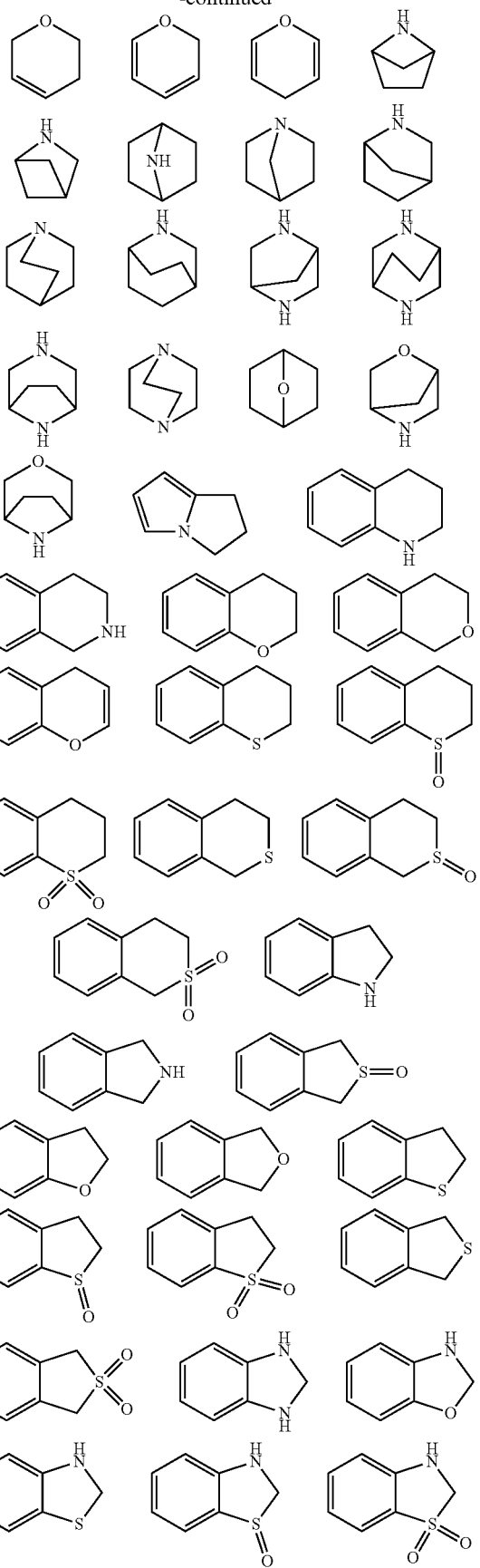

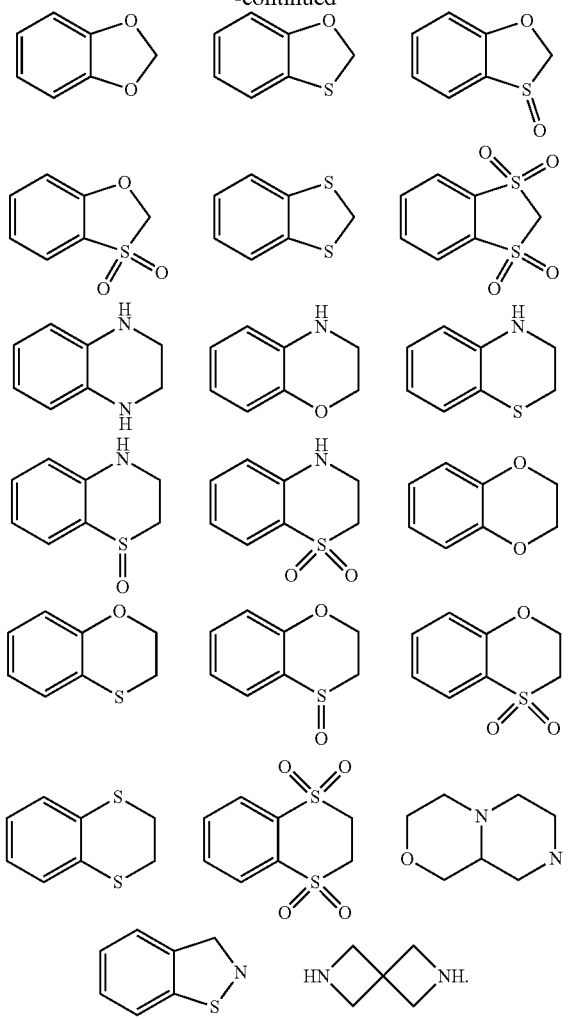
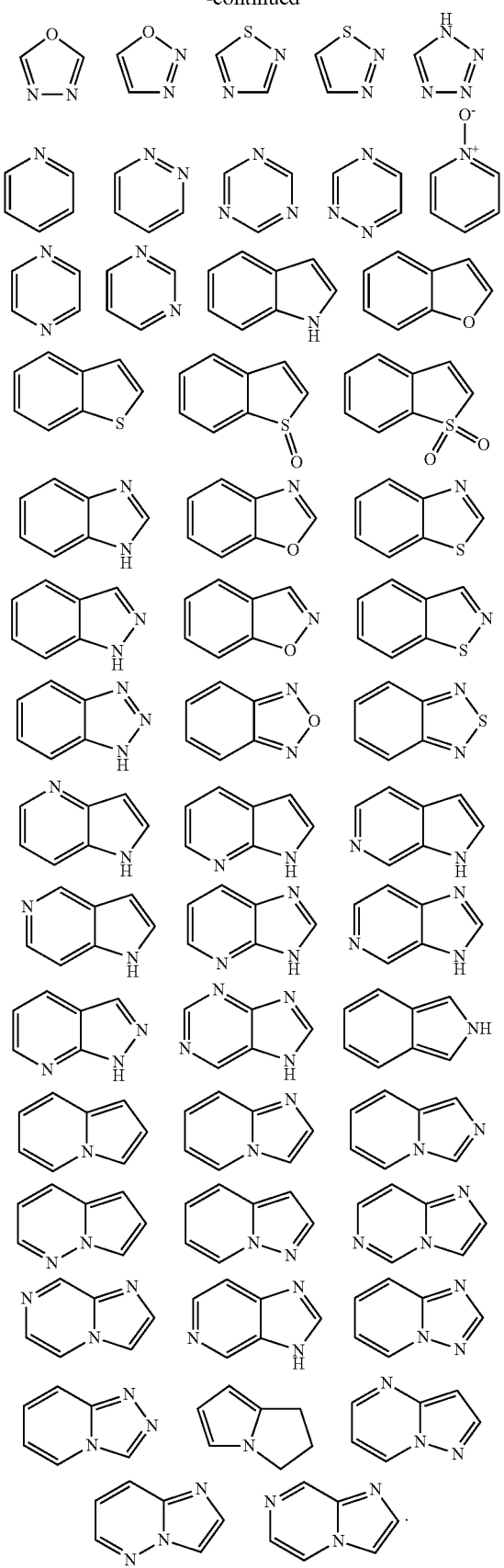

The term "heteroaryl" means a mono- or polycyclic-ring systems containing one or more heteroatoms selected from N, O or S(O)$_r$, wherein r=0, 1 or 2, consisting of 5 to 14 ring atoms wherein at least one of the heteroatoms is part of aromatic ring. The term "heteroaryl" is intended to include all the possible isomeric forms.

Thus, the term "heteroaryl" includes the following exemplary structures which are not depicted as radicals as each form are optionally attached through a covalent bond to any atom so long as appropriate valences are maintained:

Many of the terms given above may be used repeatedly in the definition of a formula or group and in each case have one of the meanings given above, independently of one another.

Suitable preparations for administering the compounds of formula 1 will be apparent to those with ordinary skill in the art and include for example tablets, pills, capsules, suppositories, lozenges, troches, solutions, syrups, elixirs, sachets, injectables, inhalatives and powders etc., preferably tablets.

Suitable tablets may be obtained, for example, by mixing one or more compounds according to formula I with known excipients, for example inert diluents, carriers, disintegrants, adjuvants, surfactants, binders and/or lubricants.

By a therapeutically effective amount for the purposes of this invention is meant a quantity of substance that is capable of obviating symptoms of illness or alleviating these symptoms, or which prolong the survival of a treated patient.

| List of Abbreviations | |
|---|---|
| ACN | acetonitrile |
| Aq. | aqueous |
| ° C. | Degree Celsius |
| CDI | 1,1'-Carbonyldiimidazole |
| CyH | cyclohexane |
| conc. | concentrated |
| DCM | dichloro methane |
| DIPEA | N,N-diisopropylethylamine |
| DMF | N,N-dimethylformamide |
| DMSO | dimethyl sulfoxide |
| ESI-MS | Electrospray ionisation mass spectrometry |
| EtOAc | ethyl acetate |
| ex | example |
| eq | equivalent |
| h | hour |
| HATU | N,N,N',N'-tetramethyl-O-(7-azabenzotriazol-1-yl)uranium hexafluorophosphate |
| HCl | Hydrochlorid acid |
| HPLC | High performance liquid chromatography |
| L | liter |
| LG | Leaving group |
| LiHMDS | Lithium-bis(trimethylsilyl)amid |
| MeOH | methanol |
| NaHCO$_3$ | sodium bicarbonate |
| min | minute |
| mL | milliliter |
| MTBE | tert-butylmethylether |
| NaH | Sodium hydride |
| Pd/C | palladium on activated carbon |
| PE | petroleum ether |
| PG | Protecting group |
| RT | room temperature (about 20° C.) |
| sat. | saturated |
| TBTU | Benzotriazolyl tetramethyluronium tetrafluoroborate |
| TEA | triethylamine |
| TFA | trifluoroacetic acid |
| THF | tetrahydrofuran |
| TLC | Thin-layer chromatography on SiO2 |

Preparation of the Compounds According to the Invention
General Synthetic Methods The compounds according to the present invention and their intermediates may be obtained using methods of synthesis which are known to the one skilled in the art and described in the literature of organic synthesis. Preferably, the compounds are obtained in analogous fashion to the methods of preparation explained more fully hereinafter, in particular as described in the experimental section. In some cases, the order in carrying out the reaction steps may be varied. Variants of the reaction methods that are known to the one skilled in the art but not described in detail here may also be used.

The general processes for preparing the compounds according to the invention will become apparent to the one skilled in the art studying the following schemes. Starting materials may be prepared by methods that are described in the literature or herein, or may be prepared in an analogous or similar manner. Any functional groups in the starting materials or intermediates may be protected using conventional protecting groups. These protecting groups may be cleaved again at a suitable stage within the reaction sequence using methods familiar to the one skilled in the art.

The compounds according to the invention are prepared by the methods of synthesis described hereinafter in which the substituents of the general formulae have the meanings given hereinbefore. These methods are intended as an illustration of the invention without restricting its subject matter and the scope of the compounds claimed to these examples. Where the preparation of starting compounds is not described, they are commercially obtainable or may be prepared analogously to known compounds or methods described herein. Substances described in the literature are prepared according to the published methods of synthesis.

Compounds of formula I may be prepared as shown in Scheme I below.

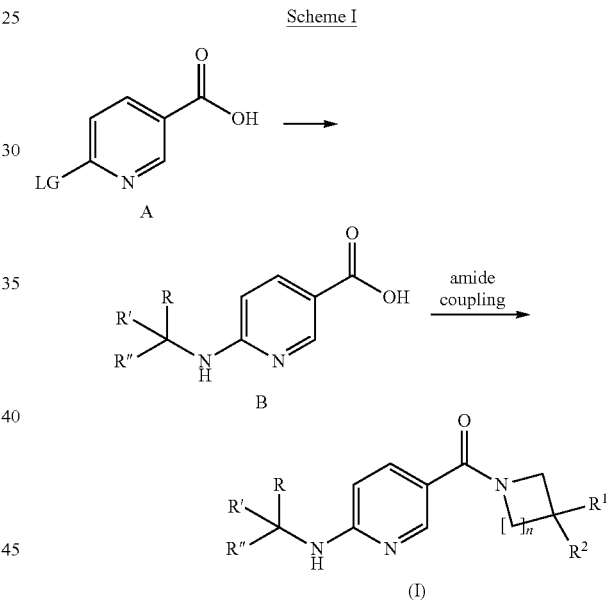

In scheme I, pyridine A, is treated with an appropriate primary amine under elevated temperature to generate pyridine B. An amide coupling (e.g. TBTU or HATU as coupling reagent) with an appropriate heterocycle as next step affords the compound of general formula (I).

Alternatively compounds of formula I may be prepared as shown in Scheme II below.

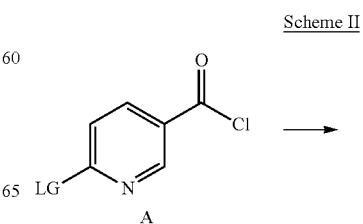

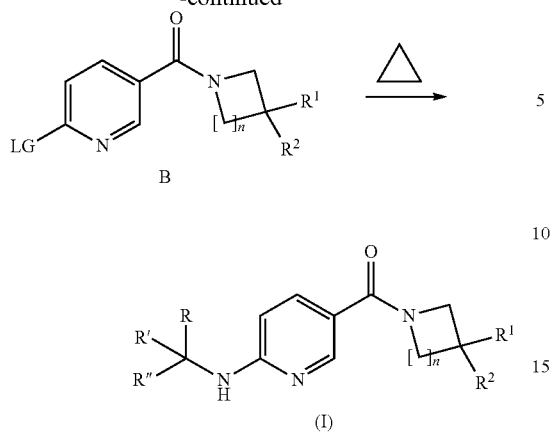

In scheme II, acid chloride A, is treated with an appropriate heterocycle to generate pyridine B. The leaving group in pyridine B can be replaced by an appropriate primary amine using elevated temperature to afford the compound of general formula (I).

Compounds of formula II may be prepared as shown in Scheme III below.

Scheme III

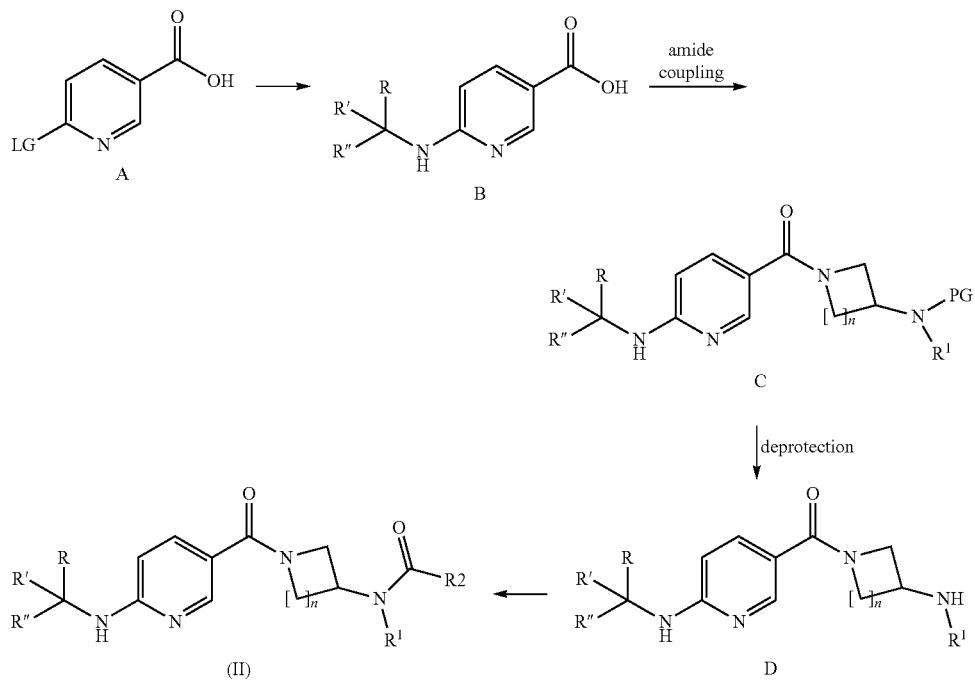

In scheme III, pyridine A, is treated with an appropriate primary amine under elevated temperature to generate pyridine B. An amide coupling (e.g. TBTU or HATU as coupling reagent) with an appropriate N-substituted and N-protected heterocycle as next step affords amide C. After deprotection (e.g. HCl or TFA for PG=BOC) another amide coupling (e.g. TBTU or HATU as coupling reagent) or urea-forming reaction (e.g. amino-carbonyl-chlorids or isocyanates as reagents) affords the compound of general formula (II).

Alternatively compounds of formula II may be prepared as shown in Scheme IV below.

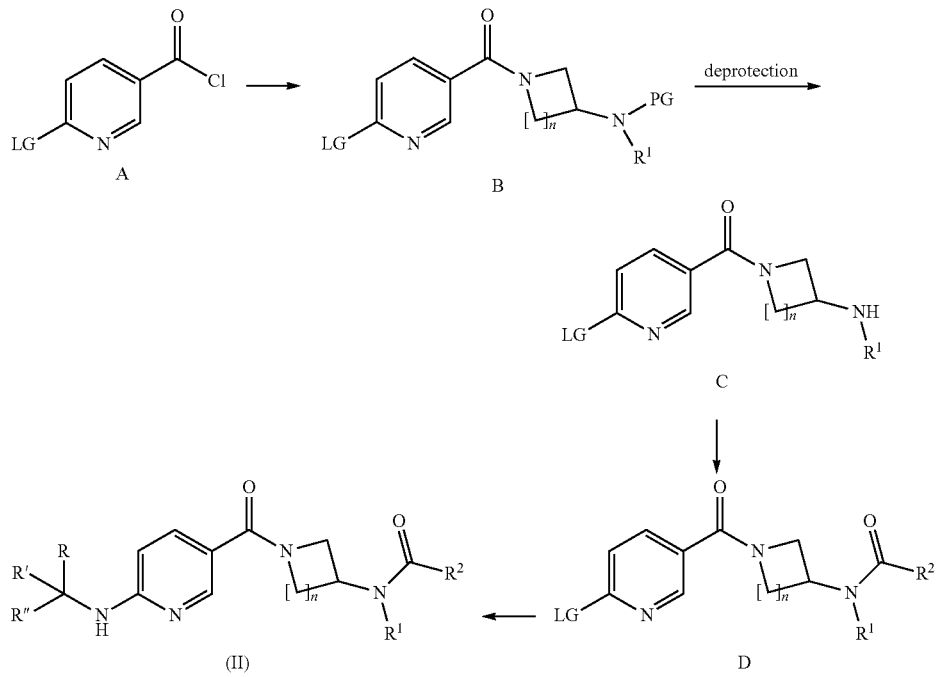

In scheme IV, acid chloride A, is treated with an appropriate N-substituted and N-protected heterocycle to generate pyridine B. After deprotection (e.g. HCl or TFA for PG=BOC) an amide coupling (e.g. TBTU or HATU as coupling reagent) affords compound D. The leaving group in compound D can be replaced by an appropriate primary amine using elevated temperature to afford the compound of general formula (II).

Features and advantages of the present invention will become apparent from the following detailed examples which illustrate the fundamentals of the invention by way of example without restricting its scope.

The terms "ambient temperature" and "room temperature" are used interchangeably and designate a temperature of about 20° C., e.g. between 19 and 24° C.

PREPARATION OF STARTING COMPOUNDS

Example I 6-(tert-Butylamino)pyridine-3-carboxylic acid

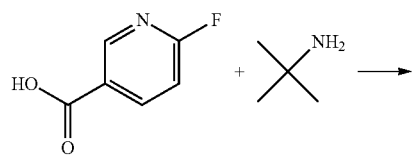

1.5 g (10.6 mmol) 6-Fluoro-nicotinic acid and 5.59 mL (53.2 mmol) tert-butylamine in 10 mL NMP are stirred at 130° C. for 68 h. The reaction mixture is acidified with HCl (4M solution) and purified by HPLC (ACN/H$_2$O/TFA).

$C_{10}H_{14}N_2O_2$ (M=194.2 g/mol)

ESI-MS: 195 [M+H]$^+$

R$_t$ (HPLC): 0.57 min (method B)

Example II tert-Butyl N-[(3S)-1-[6-(tert-butylamino)pyridine-3-carbonyl]pyrrolidin-3-yl]-N-methylcarbamate

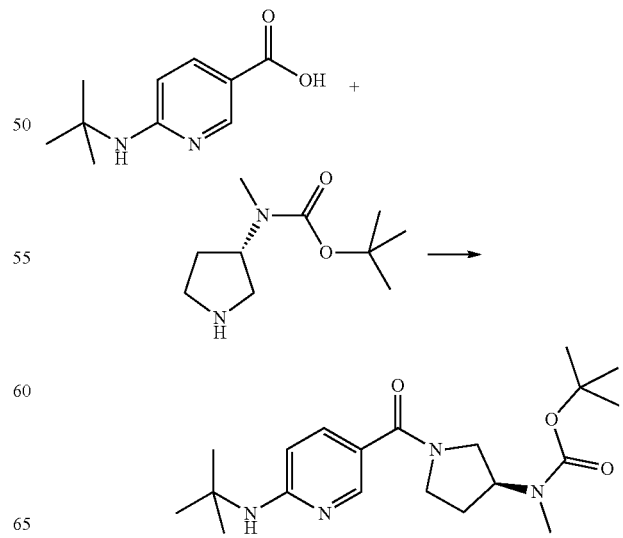

A mixture of 0.30 g (1.55 mmol) 6-(tert-butylamino)pyridine-3-carboxylic acid (example I), 0.36 g (1.78 mmol) tert-butyl N-methyl-N-[(3S)-pyrrolidin-3-yl]carbamate, 0.55 g (1.70 mmol) TBTU, 0.67 mL (3.86 mmol) DIPEA and 10 mL DMF is stirred overnight at RT. The mixture is poured into 50 mL sat. NaHCO$_3$ solution and extracted with EtOAc. The combined organic layers are dried over MgSO$_4$, filtered and the solvent is removed in vacuo.

C$_{20}$H$_{32}$N$_4$O$_3$ (M=376.5 g/mol)
ESI-MS: 377 [M+H]$^+$
R$_t$ (HPLC): 1.03 min (method C)

Example III

N-tert-Butyl-5-[(3S)-3-(methylamino)pyrrolidine-1-carbonyl]pyridin-2-amine dihydrochloride

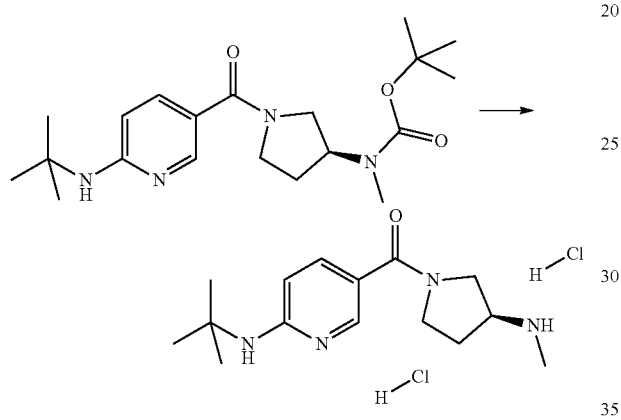

To 250 mg (0.664 mmol) tert-butyl N-[(3S)-1-[6-(tert-butylamino)pyridine-3-carbonyl]pyrrolidin-3-yl]-N-methyl-carbamate (example II) are added 10 mL HCl (4M in dioxane) and stirred for 3 h at RT. The reaction mixture is concentrated in vacuo.

C$_{15}$H$_{24}$N$_4$O*2HCl (M=349.3 g/mol)
ESI-MS: 277 [M+H]$^+$
R$_t$ (HPLC): 0.27 min (method A)

Example IV (3S)-1-(6-Fluoropyridine-3-carbonyl)-N-methylpyrrolidin-3-amine trifluoroacetic acid

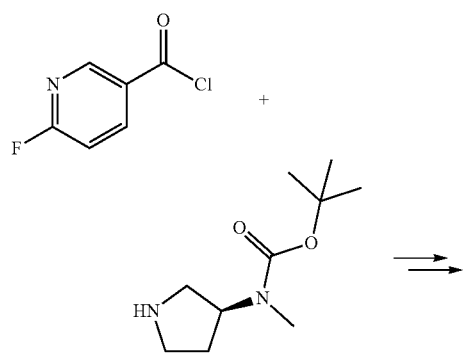

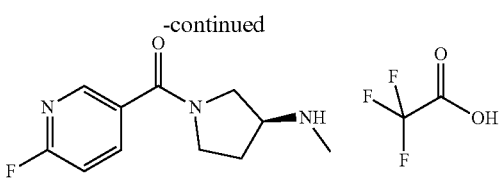

To 2.84 g (14.2 mmol) (S)-3-(N-boc-N-methylamino)pyrrolidine and 9.86 mL (70.8 mmol) TEA in 40 mL DCM are added dropwise 2.26 g (14.2 mmol) 2-fluoropyridine-5-carbonyl chloride dissolved in 30 mL DCM at 0° C. After stirring for 10 min at 0° C., the reaction mixture is filtered, the solvent is removed in vacuo and the remaining crude product purified by column chromatography (silica gel; DCM/MeOH, 99/1→90/10).

The above described product is dissolved in 25 mL DCM, then 5 mL TFA are added and the reaction mixture is stirred overnight at RT. The solvent is removed in vacuo and the crude product is used without further purification.

C$_{11}$H$_{14}$FN$_3$O*C$_2$HF$_3$O$_2$ (M=337.3 g/mol)
ESI-MS: 224 [M+H]$^+$
R$_t$ (HPLC): 0.61 min (method C)

Example V

N-[(3S)-1-(6-Fluoropyridine-3-carbonyl)pyrrolidin-3-yl]-N-methylcyclopropanecarboxamide

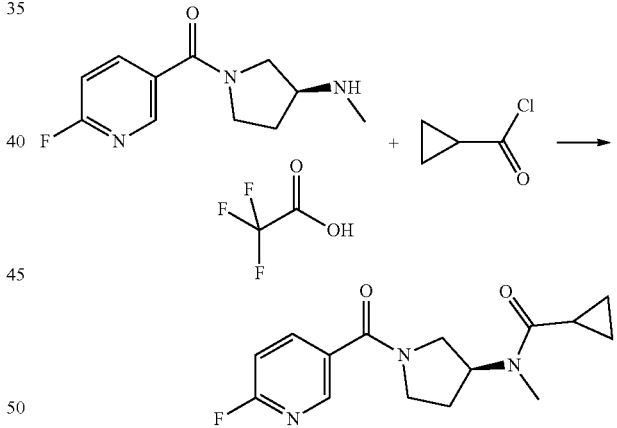

To 2.40 g (7.12 mmol) (3S)-1-(6-Fluoropyridine-3-carbonyl)-N-methylpyrrolidin-3-amine trifluoroacetic acid (example IV) and 4.95 mL (35.6 mmol) TEA in 40 mL DCM are added dropwise 0.81 g (7.83 mmol) cyclopropanecarbonyl chloride dissolved in 10 mL DCM at 0° C. After stirring for 10 min at 0° C., the reaction mixture is twice extracted with a 1:1 mixture of sat. aq. NaHCO$_3$ solution and water. Afterwards the org. layer is washed with sat. aq. NaCl solution, dried over Na$_2$SO$_4$, filtered and the solvent is removed in vacuo. The residue is purified by column chromatography (silica gel; DCM/MeOH, 99/1→90/10).

C$_{15}$H$_{18}$FN$_3$O$_2$ (M=291.3 g/mol)
ESI-MS: 292 [M+H]$^+$
R$_t$ (HPLC): 0.72 min (method A)

Example VI

N-Methyl-N-[(3S)-pyrrolidin-3-yl]acetamide hydrochloride

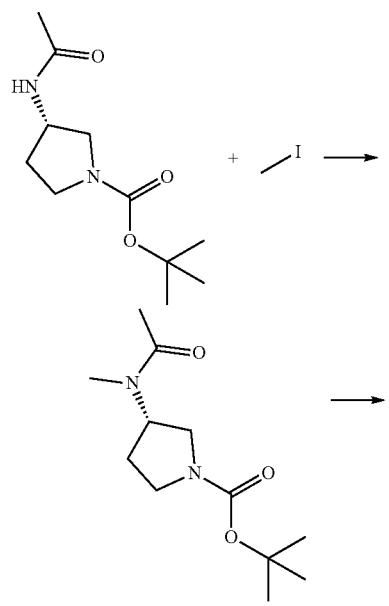

A mixture of 2.5 g (11.0 mmol) tert-butyl (3S)-3-acetamidopyrrolidine-1-carboxylate and 1 mL (15.9 mmol) iodomethane in 25 mL THF is cooled to −10° C. Then 0.75 g (18.8 mmol) NaH (60%) are added and the mixture is stirred overnight at RT. The reaction mixture is quenched with $H_2O$ and EtOAc and stirred vigorously for 5 min. The layers are separated and the $H_2O$ layer is extracted with EtOAc. The combined organic layers are dried over a phase separator cartridge and concentrated in vacuo.

Intermediate $C_{12}H_{22}N_2O_3$ (M=242.3 g/mol)
ESI-MS: 187 [M-tBu+H]$^+$
$R_t$ (HPLC): 0.82 min (method C)

The intermediate is treated with 10 mL HCl in dioxane and stirred at RT over the weekend. The obtained precipitate is filtered off, washed with dioxane and dried in vacuo to obtain the product.

$C_7H_{14}N_2O$*HCl (M=178.7 g/mol)
ESI-MS: 143 [M+H]$^+$
$R_t$ (HPLC): 0.30 min (method C)

Example VII

Example VII.1 (General Route)

N-[(3S)-1-(6-Fluoropyridine-3-carbonyl)pyrrolidin-3-yl]-N-methylacetamide

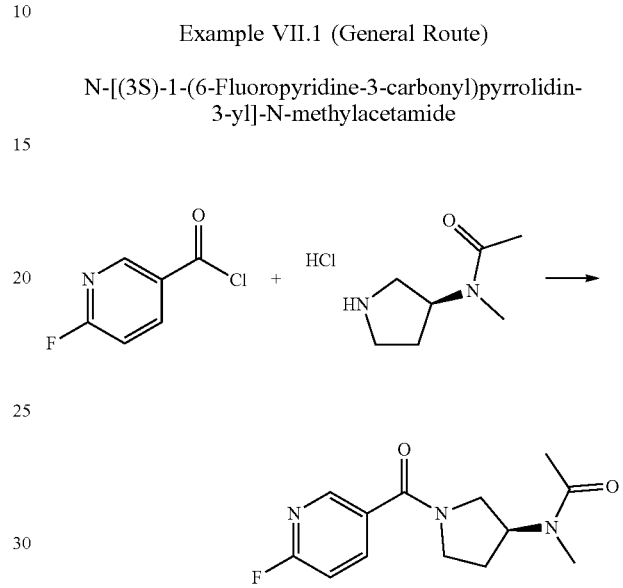

To 4.00 g (22.4 mmol) N-methyl-N-[(3S)-pyrrolidin-3-yl]acetamide hydrochloride (example VI) and 14.8 mL (106.6 mmol) TEA in 30 mL DCM are added dropwise 3.40 g (21.3 mmol) 2-fluoropyridine-5-carbonyl chloride (CAS No. 65352-94-5) dissolved in 5 mL DCM at 0° C. After stirring for 10 min at 0° C., the reaction mixture is filtered, the solvent removed in vacuo and purified by column chromatography (silica gel; DCM/MeOH, 98/2→85/15).

$C_{13}H_{16}FN_3O_2$ (M=265.3 g/mol)
ESI-MS: 266 [M+H]$^+$
$R_t$ (HPLC): 0.63 min (method A)

The following compounds are prepared according to the general procedure (example VII.1) described above:

| Ex. | Starting materials | Structure | Reaction conditions | ESI-MS | HPLC retention time (method) [min] |
|---|---|---|---|---|---|
| VII.2 | O=C(O)-pyridine-F (VIII.2) | fluoropyridine-pyrrolidine-pyrrolidinone structure | Reaction time 1 h, RT | 278 [M + H]$^+$ | 0.67 (A) |

Example VIII

Example VIII.1 (General Route)

3-[(3S)-Pyrrolidin-3-yl]-1,3-oxazolidin-2-one Hydrochloride

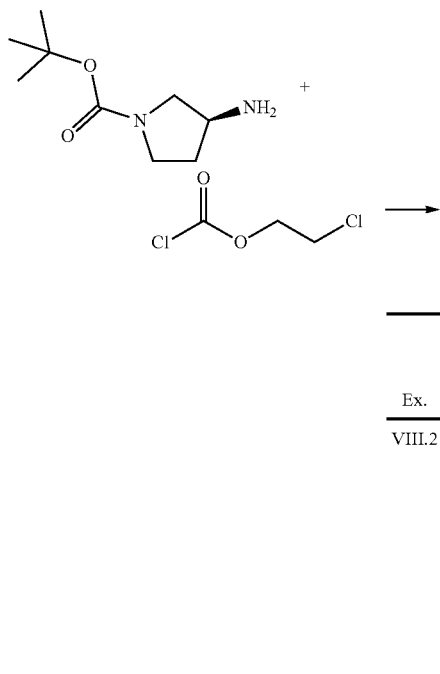

added dropwise and the reaction mixture is stirred at 00 for 1 h. 3.48 g (5.37 mmol) tetrabutylammonium hydroxide (40% in MeOH) is added and the mixture is stirred overnight at RT. The mixture is quenched with $H_2O$ and extracted with DCM. The combined organic layers are dried over a phase separator cartridge and the solvent is removed in vacuo.

The crude product is purified by column chromatography (silica gel; CyH/EtOAc).

$C_{12}H_{20}N_2O_4$ (M=256.3 g/mol)
ESI-MS: 201 [M-tBU+H]$^+$
$R_t$ (HPLC): 0.82 min (method C)

The above mentioned product is added to 2.5 mL dioxane, 5 mL (20.0 mmol) HCl in dioxane (4 mol/L) and some MeOH and the mixture is stirred overnight at RT. The solvent is removed in vacuo to obtain the product.

$C_7H_{12}N_2O_2$*HCl (M=192.6 g/mol)
ESI-MS: 157 [M+H]$^+$
$R_t$ (HPLC): 0.17 min (method C)

The following compounds are prepared according to the general procedure (example VIII.1) described above:

| Ex. | Starting materials | Structure | ESI-MS | HPLC retention time (method) [min] |
|---|---|---|---|---|
| VIII.2 | | 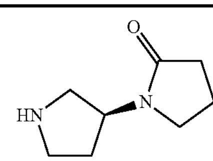 | 155 [M + H]$^+$ | 0.27 (C) |
| VIII.3 | | 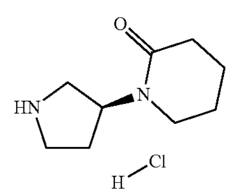 | 169 [M + H]$^+$ | 0.54 (C) |

-continued

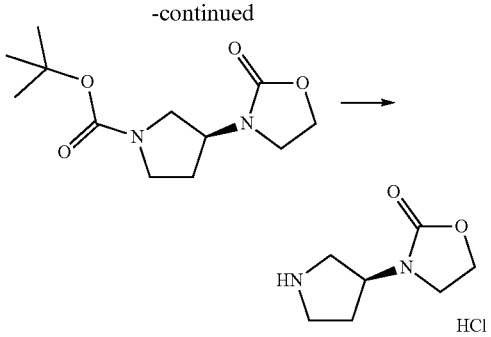

A mixture of 2.00 g (10.7 mmol) tert-butyl (3S)-3-aminopyrrolidine-1-carboxylate in 0.5 mL DCM and 4 mL NaOH (50%) is cooled to 0° C. A mixture of 1.38 g (9.66 mmol) 2-chloroethyl carbonochloridate in 0.5 mL DCM is

Example IX

N-Methyl-N-[(3S)-pyrrolidin-3-yl]pyrimidin-2-amine hydrochloride

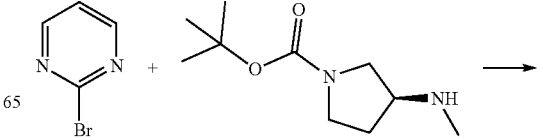

-continued

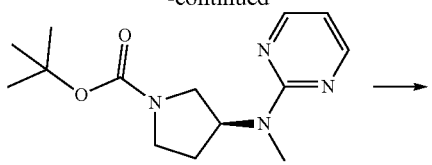

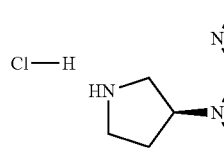

A mixture of 1.00 g (6.29 mmol) 2-bromopyrimidine, 1.51 g (7.55 mmol) tert-butyl (3S)-3-(methylamino)pyrrolidine-1-carboxylate, 3.81 mL (22.0 mmol) DIPEA and 10 mL DMF is stirred at 120° C. for 2 h. The solvent is removed in vacuo and the crude product is purified by column chromatography (silica gel; DCM/MeOH, 100/0→96/4).

$C_{14}H_{22}N_4O_2$ (M=278.4 g/mol)

ESI-MS: 279 $[M+H]^+$ $R_t$ (HPLC): 0.87 min (method A)

To the above mentioned product are added 10 mL MeOH and 4 mL HCl in dioxane (4 mol/L) and the mixture is stirred overnight at RT. The solvents are removed in vacuo to obtain the final product.

$C_9H_{14}N_4$*HCl (M=214.7 g/mol)

ESI-MS: 179 $[M+H]^+$ $R_t$ (HPLC): 0.15 min (method A)

Example X

1-{[(3S)-1-Benzylpyrrolidin-3-yl]amino}propan-2-ol

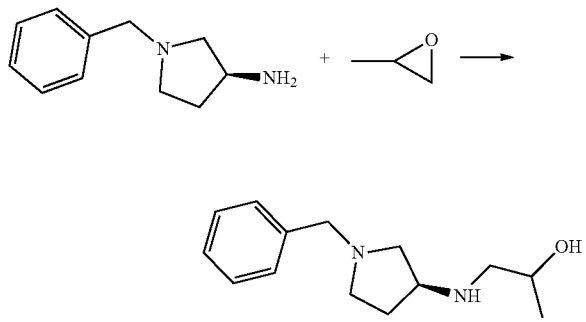

500 mg (2.84 mmol) (3S)-1-benzylpyrrolidin-3-amine in 7 mL methanol are added 0.40 mL (5.72 mmol) 2-methyloxirane and the mixture is stirred at RT for 3 days. The reaction mixture is concentrated in vacuo and purified by column chromatography (silica gel; EE/methanol, 8/2→1/1). The solvents are removed in vacuo to obtain the product.

$C_{14}H_{22}N_2O$ (M=234.3 g/mol)

ESI-MS: 235 $[M+H]^+$ $R_t$ (HPLC): 0.81 min (method C)

Example XI

3-[(3S)-1-Benzylpyrrolidin-3-yl]-5-methyl-1,3-oxazolidin-2-one

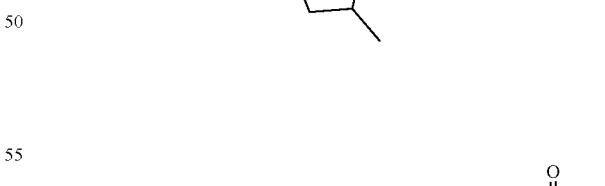

To 230 mg (0.98 mmol) 1-{[(3S)-1-benzylpyrrolidin-3-yl]amino}propan-2-ol (example X) in 10 mL DCM are added 0.51 mL (2.94 mmol) DIPEA and 191 mg (1.18 mmol) CDI and the mixture is stirred at RT for 3 h. Additional 80 mg (0.49 mmol) CDI are added and stirring is continued over night. The reaction mixture is washed with brine, dried over MgSO₄, filtered and concentrated in vacuo. The crude product is purified by HPLC (ACN/H₂O/TFA).

$C_{15}H_{20}N_2O_2$ (M=260.3 g/mol)

ESI-MS: 261 $[M+H]^+$ $R_t$ (HPLC): 0.36 min (method F)

Example XII

5-Methyl-3-[(3S)-pyrrolidin-3-yl]-1,3-oxazolidin-2-one

To 250 mg (0.96 mmol) 3-[(3S)-1-benzylpyrrolidin-3-yl]-5-methyl-1,3-oxazolidin-2-one (example XI) in 5 mL methanol are added 25 mg Pd/C (10%) and the mixture is stirred at RT over night under 50 psi hydrogen pressure. Then 0.1 mL 1M aq. HCl and 25 mg Pd/C are added and stirring is continued at 50° C. for 16 h at 50 psi hydrogen pressure. Afterwards the reaction mixture is filtered and the solvent is removed in vacuo.

$C_8H_{14}N_2O_2$ (M=170.2 g/mol)

ESI-MS: 171 [M+H]$^+$ $R_t$ (HPLC): 0.93 min (method C)

Example XIII

Example XIII.A and B tert-Butyl (3S)-3-cyano-3-methylpyrrolidine-1-carboxylate tert-Butyl (3R)-3-cyano-3-methylpyrrolidine-1-carboxylate

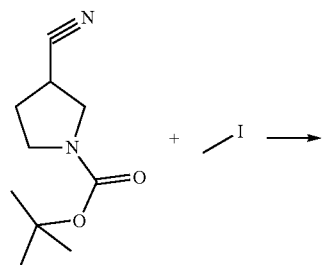

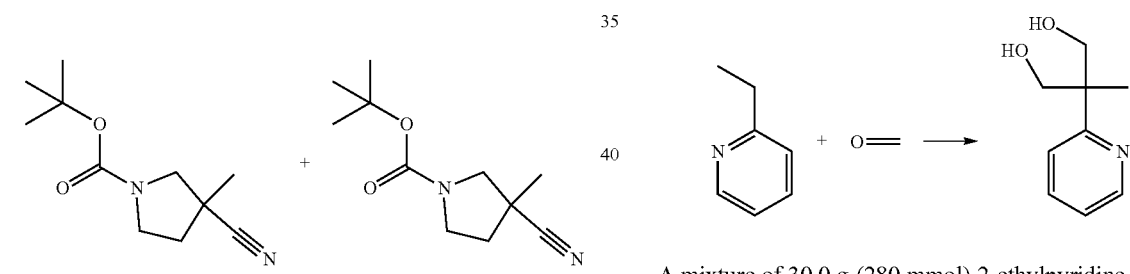

Example XIII.A
first eluting

Example XIII.B
second eluting

To a mixture of 2.70 g (13.8 mmol) tert-butyl 3-cyano-pyrrolidine-1-carboxylate and 40 mL THF are added 15.1 mL (15.1 mmol) LiHMDS at −78° C. After stirring 30 min at −78° C. 1.28 mL (20.6 mmol) iodomethane are added dropwise. The reaction mixture is stirred 30 min at −78° C. and 30 min at RT. The mixture is poured into 100 mL of a mixture of sat. aq. NH$_4$Cl solution and water (1:1) and extracted 2× with EtOAc. The organic layer is washed with brine, is dried over MgSO$_4$, filtered and the solvent is evaporated. The crude product is purified by chiral SFC (method G).

Product XIII.1.a (First Eluting):

$C_{11}H_{18}N_2O_2$ (M=210.3 g/mol)

Rt (HPLC): 2.58 min (method G)

Product XIII.1.B (Second Eluting):

$C_{11}H_{18}N_2O_2$ (M=210.3 g/mol)

Rt (HPLC): 3.65 min (method G)

Example XIV

Example XIV.A 3-methylpyrrolidine-3-carbonitrile hydrochloride

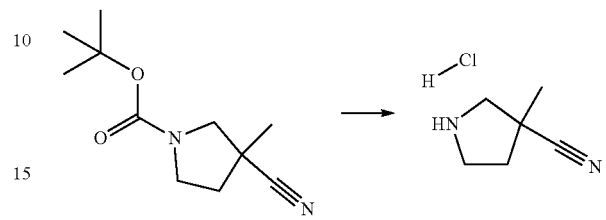

To a mixture of 1.25 g (5.95 mmol) tert-butyl 3-cyano-3-methylpyrrolidine-1-carboxylate (example XIII.A) in 10 mL dioxane are added 2.97 mL (11.9 mmol) HCl (4M in dioxane) and the mixture is stirred overnight at RT. The obtained precipitate is filtered off, washed with dioxane and dried in the air.

$C_6H_{10}N_2$*HCl (M=146.6 g/mol)

ESI-MS: 111 [M+H]$^+$ $R_f$ (TLC): 0.3 (SiO$_2$, DCM/MeOH/NH3 9/1/0.1)

Example XV

2-Methyl-2-(pyridin-2-yl)propane-1,3-diol

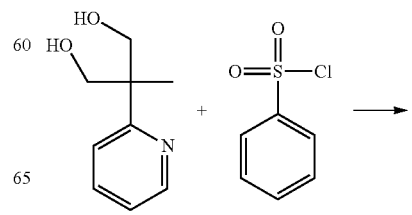

A mixture of 30.0 g (280 mmol) 2-ethylpyridine and 120 g (1.48 mol) formaldehyde is stirred in an autoclave at 150° C. over the weekend. The mixture is concentrated in vacuo.

$C_9H_{13}NO_2$ (M=167.2 g/mol)

ESI-MS: 168.6 [M+H]$^+$ $R_t$ (HPLC): 0.52 min (method C)

Example XVI

2-{1-[(Benzenesulfonyl)oxy]-2-{[(benzenesulfonyl)oxy]methyl}propan-2-yl}pyridine

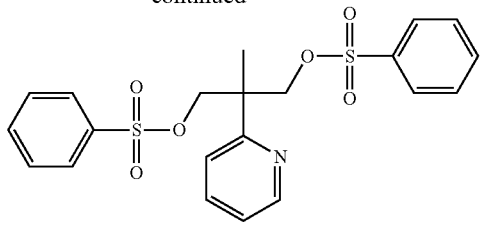

To a mixture of 5.00 g (29.9 mmol) 2-methyl-2-(pyridin-2-yl)propane-1,3-diol (example XV) in 40 mL pyridine are added 10.0 g (56.6 mmol) benzenesulfonyl chloride dropwise at 0° C. The reaction mixture is stirred at RT for 3 h. Additional 1.38 g (7.81 mmol) benzenesulfonyl chloride are added and the mixture is stirred at RT overnight.

The reaction mixture is poured into 120 mL icewater and stirred for 10 min. Then it is acidified with 5% citric acid and extracted with MTBE. The combined organic layers are concentrated in vacuo.

The filter paper and the flask are washed with DCM, the H₂O layer is extracted with DCM. The combined organic layers are concentrated in vacuo.

Both oils are combined to obtain the product.

$C_{21}H_{21}NO_6S_2$ (M=447.5 g/mol)
ESI-MS: 448.6 [M+H]⁺
$R_t$ (HPLC): 1.02 min (method C)

Example XVII 2-(1-Benzyl-3-methylazetidin-3-yl)pyridine

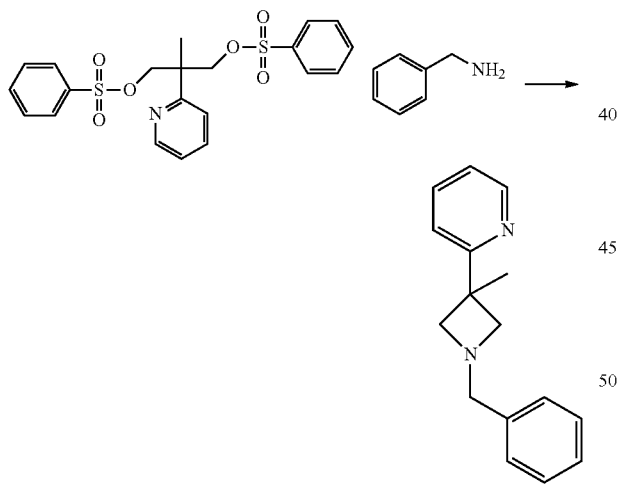

To a mixture of 28.0 g (62.6 mmol) 2-{1-[(benzenesulfonyl)oxy]-2-{[(benzenesulfonyl)oxy]methyl}propan-2-yl}pyridine (example XVI) in 250 mL ACN are added 27.1 mL (156 mmol) DIPEA and 10.3 mL (93.8 mmol) phenylmethanamine and the reaction mixture is stirred at 80° C. for 4 h and at 50° C. for 16 h. Then additional 1.03 mL (9.39 mmol) phenylmethanamine and 2.71 mL (15.6 mmol) DIPEA are added and the mixture is stirred at 80° C. for 2 h.

The solvent is removed in vacuo and the remaining residue is diluted with NaHCO₃ solution and extracted with EtOAc. The organic layers are combined and the solvent is removed in vacuo. The crude product is purified by column chromatography (silica gel; DCM/CyH/MeOH/NH₃, 7/3/0.45/0.05).

$C_{16}H_{18}N_2$ (M=238.3 g/mol)
ESI-MS: 239.6 [M+H]⁺
$R_t$ (HPLC): 0.93 min (method C)

Example XVIII 2-(3-Methylazetidin-3-yl)pyridine

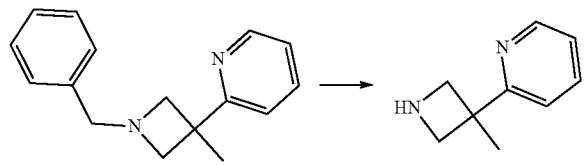 [SMILES: CC1(c2ccccn2)CN(Cc2ccccc2)C1 ; CC1(c2ccccn2)CNC1]

A mixture of 100 mg (0.42 mmol) 2-(1-benzyl-3-methylazetidin-3-yl)pyridine (example XVII), 50.0 mg Pd/C (5%), 420 μL HCl (1 mol/L) and 5 mL MeOH is hydrogenated under 50 psi H₂ pressure and 50° C. for 3.5 h. The reaction mixture is filtered and the solvent is removed in vacuo to obtain the product.

$C_9H_{12}N_2$ (M=148.2 g/mol)
ESI-MS: 149 [M+H]⁺
$R_t$ (HPLC): 0.63 min (method C)

Example IXX

N-Methyl-N-[(3R)-pyrrolidin-3-yl]acetamide hydrochloride

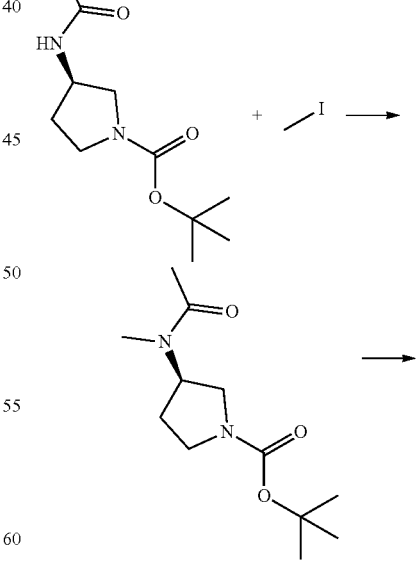

The preparation can be done analogously to example VI starting with tert-butyl (3R)-3-acetamidopyrrolidine-1-carboxylate.

$C_7H_{14}N_2O$*HCl (M=178.7 g/mol)
ESI-MS: 143 [M+H]⁺

PREPARATION OF FINAL COMPOUNDS

Example 1

Example 1.1 (General Route)

N-[(3S)-1-[6-(tert-Butylamino)pyridine-3-carbonyl]pyrrolidin-3-yl]-N-methylcyclobutanecarboxamide

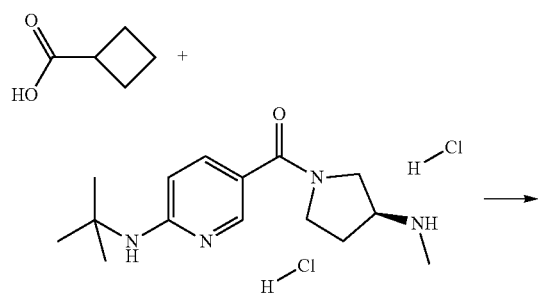

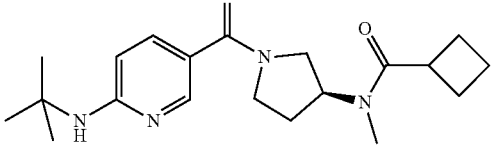

A mixture of 16.0 mg (0.16 mmol) cyclobutanecarboxylic acid, 61.4 mg (0.18 mmol) N-tert-butyl-5-[(3S)-3-(methylamino)pyrrolidine-1-carbonyl]pyridin-2-amine dihydrochloride (example III), 59.0 mg (0.18 mmol) TBTU, 0.04 mL (0.24 mmol) DIPEA and 2 mL DMF is stirred at RT for 15 h. The mixture is filtered and purified by HPLC (ACN/H$_2$O/NH$_4$OH).

$C_{20}H_{30}N_4O_2$ (M=358.5 g/mol)

ESI-MS: 359 [M+H]$^+$

R$_t$ (HPLC): 0.71 min (method A)

The following compounds are prepared according to the general procedure (example 1.1) described above:

| Ex. | Starting materials | Structure | Reaction conditions | ESI-MS | HPLC retention time (method) [min] |
|---|---|---|---|---|---|
| 1.2 | (3,3-difluorocyclobutanecarboxylic acid) | III | | 395 [M + H]$^+$ | 0.71 (A) |
| 1.3 | ((S)-tetrahydrofuran-2-carboxylic acid) | III | | 375 [M + H]$^+$ | 0.86 (C) |
| 1.4 | (5-chlorothiophene-2-carboxylic acid) | III | HPLC (ACN/H$_2$O/TFA) | 421 [M + H]$^+$ | 0.56 (E) |
| 1.5 | (cyclopropanecarboxylic acid) | III | | 345 [M + H]$^+$ | 0.67 (A) |
| 1.6 | I.1 | VIII.1 | | 333 [M + H]$^+$ | 0.60 (A) |

-continued

| Ex. | Starting materials | | Structure | Reaction conditions | ESI-MS | HPLC retention time (method) [min] |
|---|---|---|---|---|---|---|
| 1.7 | (pyrazole-CF3-COOH) | III | 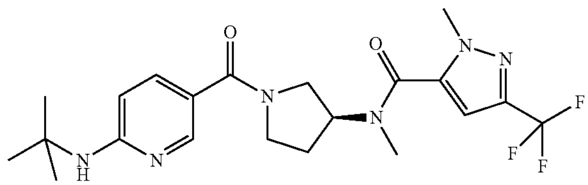 [SMILES: CN(C(=O)c1cc(C(F)(F)F)nn1C)[C@H]1CCN(C(=O)c2ccc(NC(C)(C)C)nc2)C1] | HPLC (ACN/H2O/ TFA) | 453 [M + H]+ | 0.55 (E) |
| 1.8 | (cyclopropyl-CN-COOH) | III | 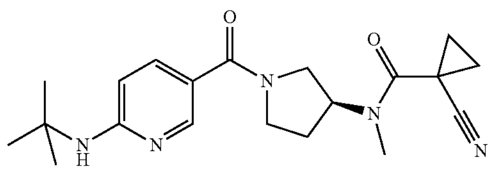 [SMILES: CN(C(=O)C1(C#N)CC1)[C@H]1CCN(C(=O)c2ccc(NC(C)(C)C)nc2)C1] | | 370 [M + H]+ | 0.67 (A) |
| 1.9 | I.1 | VIII.2 | 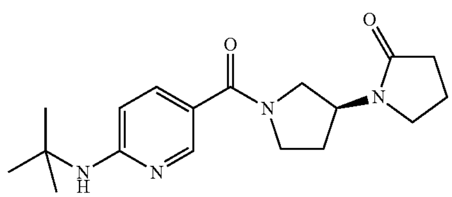 [SMILES: CC(C)(C)Nc1ccc(C(=O)N2CC[C@H](N3CCCC3=O)C2)cn1] | HPLC (ACN/H2O/ TFA) | 331 [M + H]+ | 0.63 (A) |
| 1.10 | (tetrahydrofuran-COOH) | III | 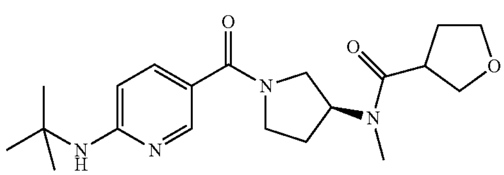 [SMILES: CN(C(=O)C1CCOC1)[C@H]1CCN(C(=O)c2ccc(NC(C)(C)C)nc2)C1] | | 375 [M + H]+ | 0.83 (C) |
| 1.11 | (4-F-benzoic acid) | III | 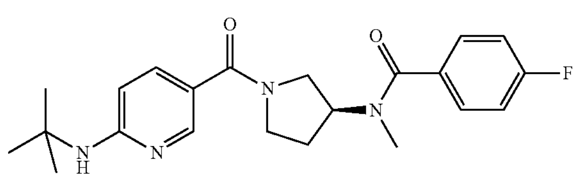 [SMILES: CN(C(=O)c1ccc(F)cc1)[C@H]1CCN(C(=O)c2ccc(NC(C)(C)C)nc2)C1] | HPLC (ACN/H2O/ TFA) | 399 [M + H]+ | 0.49 (E) |
| 1.12 | (methyl-pyrazole-COOH) | III | 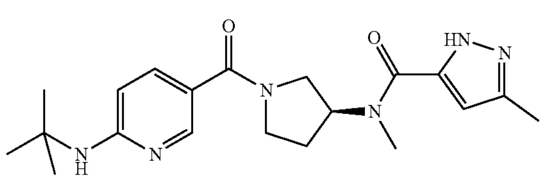 [SMILES: Cc1cc(C(=O)N(C)[C@H]2CCN(C(=O)c3ccc(NC(C)(C)C)nc3)C2)[nH]n1] | | 385 [M + H]+ | 0.58 (D) |
| 1.13 | I | IX.1 | 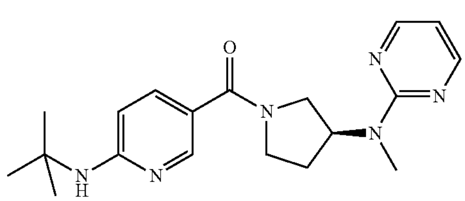 [SMILES: CN(c1ncccn1)[C@H]1CCN(C(=O)c2ccc(NC(C)(C)C)nc2)C1] | | 355 [M + H]+ | 0.73 (D) |

-continued

| Ex. | Starting materials | | Structure | Reaction conditions | ESI-MS | HPLC retention time (method) [min] |
|---|---|---|---|---|---|---|
| 1.14 | I | VIII.3 | 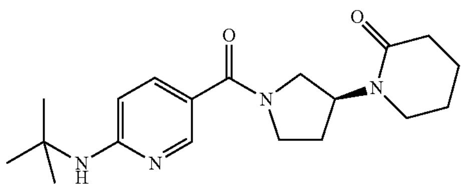 [SMILES: CC(C)(C)Nc1ccc(C(=O)N2CC[C@H](N3CCCCC3=O)C2)cn1] | RT, 3 h | 345 [M + H]⁺ | 0.84 (C) |
| 1.15 | OH (tetrahydrofuran-2-carboxylic acid) | III | 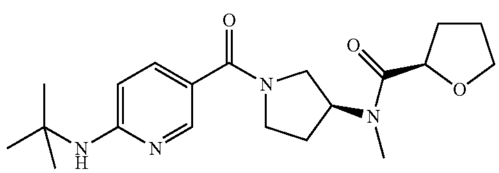 [SMILES: CN(C(=O)[C@H]1CCCO1)[C@H]1CCN(C(=O)c2ccc(NC(C)(C)C)nc2)C1] | | 375 [M + H]⁺ | 0.84 (C) |
| 1.16 | OH (morpholinoacetic acid) | III | 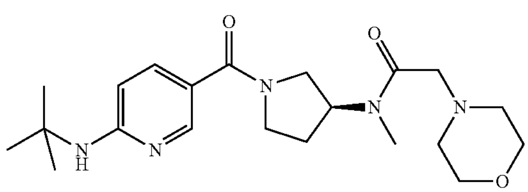 [SMILES: CN(C(=O)CN1CCOCC1)[C@H]1CCN(C(=O)c2ccc(NC(C)(C)C)nc2)C1] | | 404 [M + H]⁺ | 0.57 (D) |

Example 2

Example 2.1 (General Route)

N-Methyl-N-[(3S)-1-{6-[(1-methylcyclobutyl)amino]pyridine-3-carbonyl}pyrrolidin-3-yl]cyclopropanecarboxamide

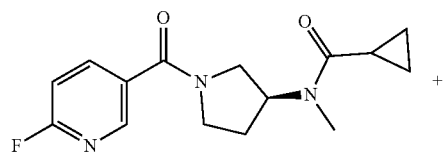

+

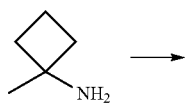

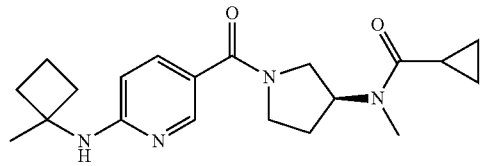

A mixture of 50.0 mg (0.17 mmol) N-[(3S)-1-(6-fluoropyridine-3-carbonyl)pyrrolidin-3-yl]-N-methylcyclopropanecarboxamide (example V), 29.2 mg (0.34 mmol) 1-methylcyclobutan-1-amine, 147 μL (1.00 mmol) DIPEA and 1 mL DMSO is stirred overnight at 120° C.

The mixture is diluted with ACN, filtered and purified by HPLC (ACN/H₂O/NH₄OH).

$C_{21}H_{30}N_4O_2$ (M=356.5 g/mol)

ESI-MS: 357 [M+H]⁺

$R_t$ (HPLC): 0.88 min (method C)

The following compounds are prepared according to the general procedure (example 2.1) described above:

| Ex. | Starting materials | Structure | Reaction conditions | ESI-MS | HPLC retention time (method) [min] |
|---|---|---|---|---|---|
| 2.2 | VII.1 HCl 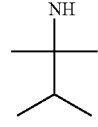 | 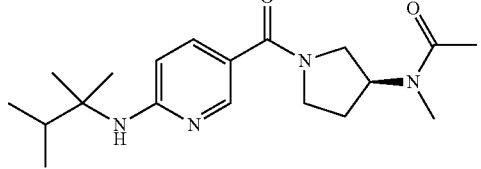 | 130° C.; Solvent: NMP, HPLC (ACN/H₂O/TFA) | 347 [M + H]⁺ | 0.90 (C) |
| 2.3 | V.1  | 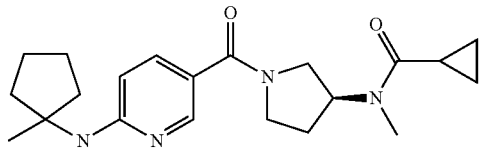 | After one night additional amine (2 eq) and DIPEA (5 eq), 120° C. overnight | 371 [M + H]⁺ | 0.92 (C) |
| 2.4 | VII.2  Cl—H | 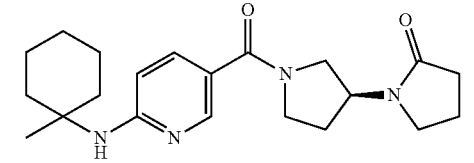 [SMILES: CC1(Nc2ccc(C(=O)N3CC[C@H](N4CCCC4=O)C3)cn2)CCCCC1] | After two night at 120° C. additional amine (2 eq) and DIPEA (5 eq) then 140° C. overnight | 371 [M + H]⁺ | 0.93 (C) |
| 2.5 | V.1 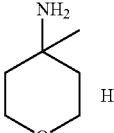 HCl | 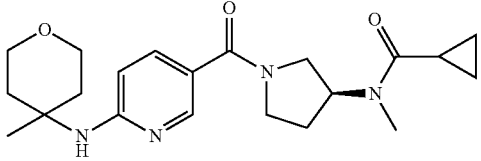 [SMILES: CN(C(=O)C1CC1)[C@H]1CCN(C(=O)c2ccc(NC3(C)CCOCC3)nc2)C1] | After two night at 120° C. additional amine (2 eq) and DIPEA (5 eq) then 140° C. overnight | 387 [M + H]⁺ | 0.80 (C) |
| 2.6 | V.1 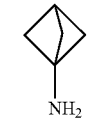 HCl | 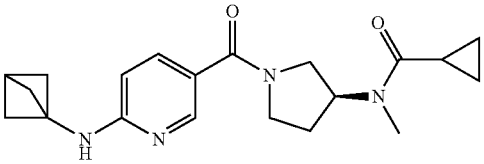 [SMILES: CN(C(=O)C1CC1)[C@H]1CCN(C(=O)c2ccc(NC34CC(C3)C4)nc2)C1] | | 355 [M + H]⁺ | 0.86 (C) |

Example 3

Example 3.1 (General Route)

N-[(3S)-1-{6-[(4-Hydroxy-2-methylbutan-2-yl)amino]pyridine-3-carbonyl}pyrrolidin-3-yl]-N-methylacetamide

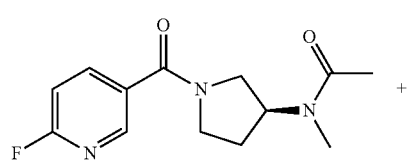 +

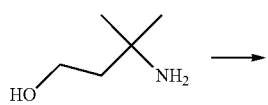 →

-continued

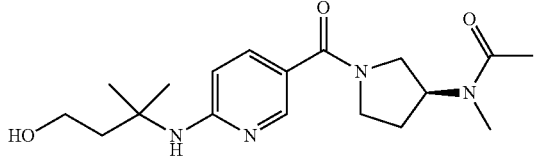

A mixture of 50.0 mg (0.19 mmol) N-[(3S)-1-(6-Fluoro-pyridine-3-carbonyl)pyrrolidin-3-yl]-N-methylacetamide (example VII.1), 77.8 mg (0.75 mmol) 3-amino-3-methylbutan-1-ol and 1 mL NMP is stirred overnight at 130° C. After cooling down the reaction mixture is filtered and purified by HPLC (ACN/H₂O/NH₄OH).

$C_{18}H_{28}N_4O_3$ (M=348.4 g/mol)

ESI-MS: 349 [M+H]⁺

$R_t$ (HPLC): 0.56 min (method A)

The following compounds are prepared according to the general procedure (example 3.1) described above:

| Ex. | Starting materials | Structure | Reaction conditions | ESI-MS | HPLC retention time (method) [min] |
|---|---|---|---|---|---|
| 3.2 | VII.1 | 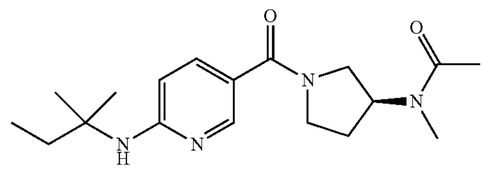 [SMILES: CCC(C)(C)Nc1ccc(C(=O)N2CC[C@H](N(C)C(C)=O)C2)cn1] | HPLC (ACN/H$_2$O/ TFA) | 333 [M + H]$^+$ | 0.65 (A) |
| 3.3 | VII.1 | 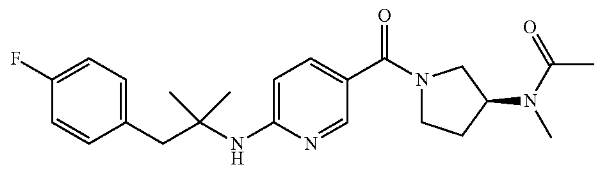 [SMILES: CC(=O)N(C)[C@H]1CCN(C(=O)c2ccc(NC(C)(C)Cc3ccc(F)cc3)nc2)C1] | HPLC (ACN/H$_2$O/ TFA) | 413 [M + H]$^+$ | 0.76 (A) |
| 3.4 | VII.1 | 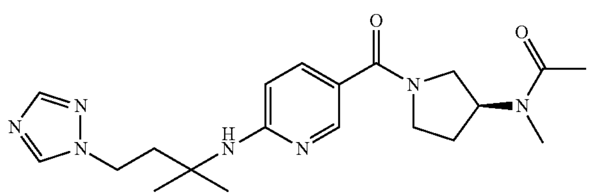 [SMILES: CC(=O)N(C)[C@H]1CCN(C(=O)c2ccc(NC(C)(C)CCn3cncn3)nc2)C1] | | 400 [M + H]$^+$ | 0.58 (C) |

Example 4

Example 4.1 (General Route)

N-[(3S)-1-[6-(tert-Butylamino)pyridine-3-carbonyl]pyrrolidin-3-yl]-N-methylmorpholine-4-carboxamide

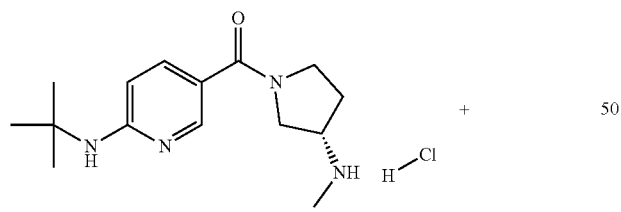

+

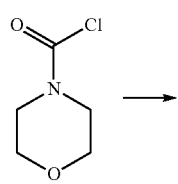

→

-continued

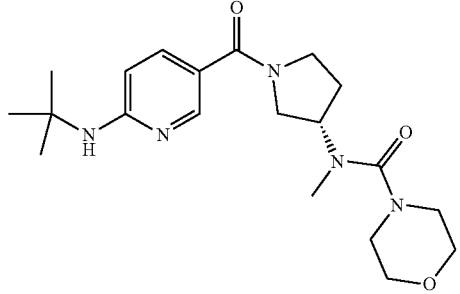

To a mixture of 30.0 mg (0.10 mmol) N-tert-butyl-5-[(3S)-3-(methylamino)pyrrolidine-1-carbonyl]pyridin-2-amine hydrochloride (example III) and 66.0 μL (0.38 mmol) DIPEA in 1 mL DMF are added 22.0 μL morpholine-4-carbonyl chloride and the mixture is stirred at RT over the weekend. The reaction mixture is purified by HPLC (ACN/H$_2$O/NH$_4$OH).

C$_{20}$H$_{31}$N$_5$O$_3$ (M=389.5 g/mol)

ESI-MS: 390 [M+H]$^+$

R$_t$ (HPLC): 0.6 min (method D)

The following compound is prepared according to the general procedure (example 4.1) described above:

| Ex. | Starting materials | Structure | ESI-MS | HPLC retention time (method) [min] |
|---|---|---|---|---|
| 4.2 | III 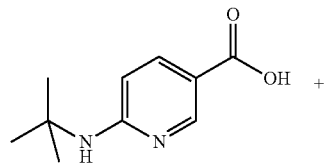 | 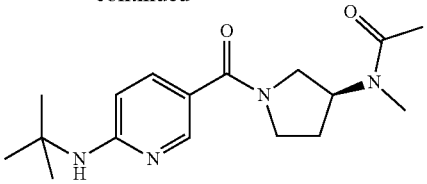 | 403.5 [M + H]⁺ | 0.60 (D) |

Example 5

Example 5.1 (General Route)

N-[(3S)-1-[6-(tert-Butylamino)pyridine-3-carbonyl]pyrrolidin-3-yl]-N-methylacetamide

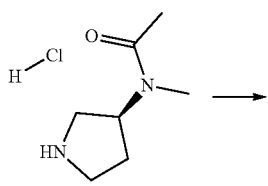

To a mixture of 2.20 g (11.4 mmol) 6-(tert-Butylamino)pyridine-3-carboxylic acid (example I), 2.43 g (13.6 mmol) N-Methyl-N-[(3S)-pyrrolidin-3-yl]acetamide hydrochloride (example VI) and 7.85 mL (45.4 mmol) DIPEA in 20 mL DMF are added 3.83 g (11.9 mmol) TBTU and the reaction mixture is stirred at RT for 10 min. The solvent is partially removed in vacuo and the remaining mixture is purified by HPLC (ACN/H$_2$O/NH$_4$OH).

$C_{17}H_{26}N_4O_2$ (M=318.4 g/mol)

ESI-MS: 319 [M+H]⁺

R$_t$ (HPLC): 0.64 min (method B)

The following compound is prepared according to the general procedure (example 5.1) described above:

| Ex. | Starting materials | Structure | ESI-MS | HPLC retention time (method) [min] |
|---|---|---|---|---|
| 5.2 | I  IXX | 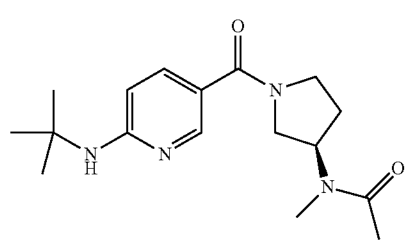 [SMILES: CC(=O)N(C)[C@@H]1CCN(C(=O)c2ccc(NC(C)(C)C)nc2)C1] | 319 [M + H]⁺ | 0.64 (B) |

Example 6

Example 6.1

3-[(3S)-1-[6-(tert-Butylamino)pyridine-3-carbonyl]pyrrolidin-3-yl]-5-methyl-1,3-oxazolidin-2-one

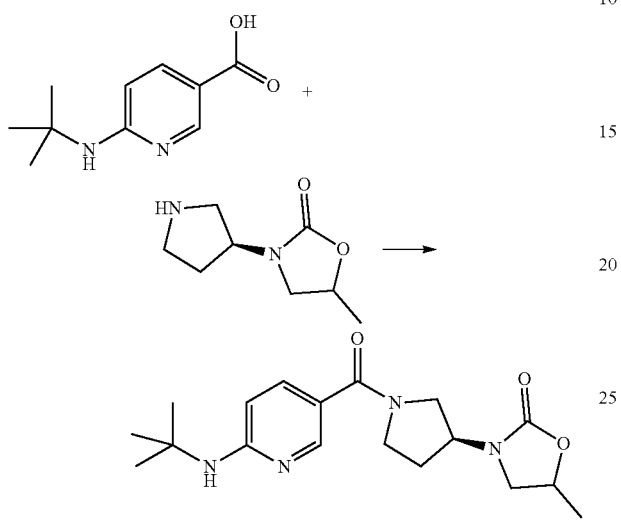

A mixture of 80.0 mg (0.41 mmol) 6-(tert-butylamino)pyridine-3-carboxylic acid (example I.1), 80.0 mg (0.47 mmol) 5-methyl-3-[(3S)-pyrrolidin-3-yl]-1,3-oxazolidin-2-one (example XII.1), 145 mg (0.45 mmol) TBTU, 0.18 mL (1.03 mmol) DIPEA and 3 mL DMF is stirred at RT overnight. The mixture is poured into 100 mL sat. aq. NaHCO₃ solution and extracted 3× with EtOAc. The combined organic layer is dried over MgSO₄, filtered and the solvent is removed in vacuo. The crude product is purified by HPLC (ACN/H₂O/NH₄OH) and freeze dried to obtain the product.

$C_{18}H_{26}N_4O_3$ (M=346.4 g/mol)
ESI-MS: 347 [M+H]⁺
$R_t$ (HPLC): 0.84 min (method C)

Example 7

1-[6-(tert-Butylamino)pyridine-3-carbonyl]-3-methylpyrrolidine-3-carbonitrile

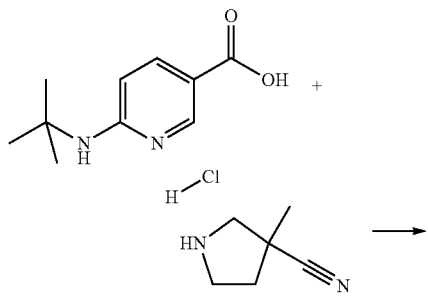

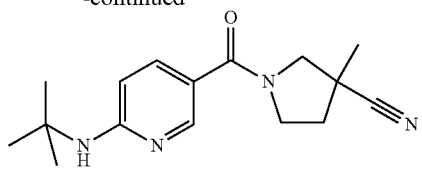

To a mixture of 9.71 mg (0.05 mmol) 6-(tert-butylamino)pyridine-3-carboxylic acid (example I.1), 7.33 mg (0.05 mmol) 3-methylpyrrolidine-3-carbonitrile hydrochloride (example XIV.A), 28.4 µL (0.17 mmol) DIPEA and 0.5 mL DMF are added 20.9 mg (0.06 mmol) HATU and the reaction mixture is stirred overnight at RT. The mixture is filtered and purified by HPLC (ACN/H₂O/NH₄OH) to obtain the enantiomerically pure product.

$C_{16}H_{22}N_4O$ (M=286.4 g/mol)
ESI-MS: 287 [M+H]⁺
$R_t$ (HPLC): 0.65 min (method D)

Example 8

N-tert-Butyl-5-[3-methyl-3-(pyridin-2-yl)azetidine-1-carbonyl]pyridin-2-amine

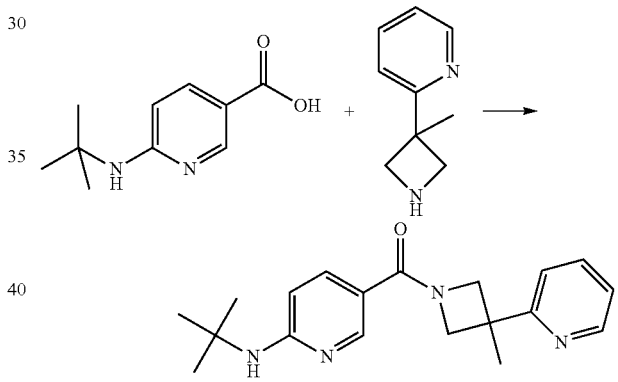

To a mixture of 38.9 mg (0.10 mmol) 6-(tert-butylamino)pyridine-3-carboxylic acid (50%; example I.1) in 1 mL DMF are added 35.3 mg (110 µmol) TBTU and 43.0 µL (250 µmol) DIPEA and the mixture is stirred at RT. After stirring for 10 min at RT 17.8 mg (120 µmol) 2-(3-methylazetidin-3-yl)pyridine (example XVIII.1) are added and the mixture is stirred overnight at RT.

The reaction mixture is purified by HPLC (ACN/H₂O/NH₄OH) to obtain the product.

$C_{19}H_{24}N_4O$ (M=324.4 g/mol)
ESI-MS: 325 [M+H]⁺
$R_t$ (HPLC): 0.73 min (method H)

Analytical HPLC Methods

| | Method A | | |
|---|---|---|---|
| time (min) | Vol % water (incl. 0.1% TFA) | Vol % ACN | Flow [mL/min] |
| 0.00 | 97 | 3 | 2.2 |
| 0.20 | 97 | 3 | 2.2 |

-continued

Method A

| time (min) | Vol % water (incl. 0.1% TFA) | Vol % ACN | Flow [mL/min] |
|---|---|---|---|
| 1.20 | 0 | 100 | 2.2 |
| 1.25 | 0 | 100 | 3.0 |
| 1.40 | 0 | 100 | 3.0 |

Analytical column: Sunfire (Waters) 2.5 µm; 3.0 × 30 mm; column temperature: 60° C.

Method B

| time (min) | Vol % water (incl. 0.1% TFA) | Vol % ACN | Flow [mL/min] |
|---|---|---|---|
| 0.00 | 97 | 3 | 2.2 |
| 0.20 | 97 | 3 | 2.2 |
| 1.20 | 0 | 100 | 2.2 |
| 1.25 | 0 | 100 | 3.0 |
| 1.40 | 0 | 100 | 3.0 |

Analytical column: Stable Bond (Agilent) 1.8 µm; 3.0 × 30 mm; column temperature: 60° C.

Method C

| time (min) | Vol % water (incl. 0.1% NH$_4$OH) | Vol % ACN | Flow [mL/min] |
|---|---|---|---|
| 0.00 | 97 | 3 | 2.2 |
| 0.20 | 97 | 3 | 2.2 |
| 1.20 | 0 | 100 | 2.2 |
| 1.25 | 0 | 100 | 3 |
| 1.40 | 0 | 100 | 3 |

Analytical column: XBridge (Waters) 2.5 µm; 3.0 × 30 mm; column temperature: 60° C.

Method D

| Gradient/Solvent Time [min] | % Sol [Water 0.1% NH3] | % Sol [Acetonitrile] | Flow [ml/min] | Temp [° C.] |
|---|---|---|---|---|
| 0.0 | 95.0 | 5.0 | 1.5 | 60.0 |
| 1.3 | 0.0 | 100.0 | 1.5 | 60.0 |
| 1.5 | 0.0 | 100.0 | 1.5 | 60.0 |
| 1.6 | 95.0 | 5.0 | 1.5 | 60.0 |

Preparative column: XBridge (Waters) C18_3.0 × 30 mm_2.5 µm

Method E

| Gradient/Solvent Time [min] | % Sol [Water 0.1% TFA (v/v)] | % Sol [Acetonitrile 0.08% TFA (v/v)] | Flow [ml/min] | Temp [° C.] |
|---|---|---|---|---|
| 0.0 | 95.0 | 5.0 | 1.5 | 60.0 |
| 1.3 | 0.0 | 100.0 | 1.5 | 60.0 |
| 1.5 | 0.0 | 100.0 | 1.5 | 60.0 |
| 1.6 | 95.0 | 5.0 | 1.5 | 60.0 |

Preparative column: Sunfire (Waters) C18_3.0 × 30 mm_2.5 µm

Method F

| Gradient/Solvent Time [min] | % Sol [Water 0.1% FA (v/v)] | % Sol [Acetonitrile] | Flow [ml/min] | Temp [° C.] |
|---|---|---|---|---|
| 0.0 | 97.0 | 3.0 | 2.2 | 60.0 |
| 0.2 | 97.0 | 3.0 | 2.2 | 60.0 |
| 1.2 | 0.0 | 100.0 | 2.2 | 60.0 |
| 1.25 | 0.0 | 100.0 | 3.0 | 60.0 |
| 1.4 | 0.0 | 100.0 | 3.0 | 60.0 |

Sunfire C18_3.0 × 30 mm_2.5 µm (Waters)

Method G

| Gradient/Solvent Time [min] | % Sol [scCO2] | % Sol [IPA 20 mM NH3] | Flow [ml/min] | Temp [° C.] | Back pressure [PSI] |
|---|---|---|---|---|---|
| 0.0 | 95.0 | 5.0 | 4.0 | 40.0 | 2175.0 |
| 10.0 | 95.0 | 5.0 | 4.0 | 40.0 | 2175.0 |

CHIRAL ART ® Cellulose SC_4.6 × 250 mm_5 µm (YMC)

Method H

| Gradient/Solvent Time [min] | % Sol [Water 0.1% NH3] | % Sol [Acetonitrile] | Flow [ml/min] | Temp [° C.] |
|---|---|---|---|---|
| 0.0 | 95.0 | 5.0 | 1.5 | 60.0 |
| 1.3 | 0.0 | 100.0 | 1.5 | 60.0 |
| 1.5 | 0.0 | 100.0 | 1.5 | 60.0 |
| 1.6 | 95.0 | 5.0 | 1.5 | 60.0 |

XBridge C18_3.0 × 30 mm_2.5 µm (Waters)

Description of Biological Properties

Vanin-1 Enzymatic Assay:

The test compounds are dissolved in 100% DMSO at a concentration of 10 mM and in a first step diluted in DMSO to a concentration of 5 mM, followed by serial dilution steps in 100% DMSO. Dilution factor and number of dilution steps may vary according to needs. Typically 8 different concentrations by 1:5 dilutions are prepared, a further intermediate dilutions of the substances is carried out with assay buffer resulting in 1% final DMSO concentration in the assay.

0.1 nM of FLAG-tagged Vanin-1 (AA 22-493, T26I, produced internally) and test compounds are incubated at room temperature for 20 minutes in assay buffer (1 mM DTT, 0.0025% Brij-35, 50 mM HEPES, pH7.5). D-Pantethine (Sigma, Cat #P2125-5G) in assay buffer is added (final concentration 3 µM) and incubated for additional 30 minutes at room temperature. Total assay volume typically is 40 µl but might be adjusted according to needs. Reaction is stopped by adding equal volume of stop solution as the reaction mixture to reach 100 nM HD-pantothenic acid (as an internal standard) and 1% TFA. Assay plates are centrifuged for 2 minutes and the formation of pantothenic acid is detected by RapidFire Mass Spectrometry (mobile phase A: 0.1% formic acid and 0.01% trifluoroacetic acid in water; mobile phase B: 47.5% acetonitrile, 47.5% methanol, 0.1% formic acid and 0.01% trifluoroacetic acid in water) using a C18, 12 µL cartridge (Agilent Cat #G9205A).

The values given in Table I result from measurements of one or more samples. In case of multiple measurements the geometric mean values are given.

Human Whole Blood assay:

Panteteinase (vanin) converts panteheine into pantothenic acid and cysteamine. Accordingly, in the described protocol vanin activity is quantified by formation of pantothenic acid after pantetheine supplementation via pantethine. The assay is applicable to identify vanin inhibitors. Compound stocks are dissolved in DMSO at 10 mM. Further dilutions are performed in RPMI 1640 medium (Gibco, #A-10491-01) and final concentrations in the assay are 0.032 nM-500 nM.

Human blood is drawn into a blood bag (1% heparin, 50 I.E./mL). Blood is aliquoted into cavities of 96-deep-well plates at 290 µL and mixed with 10 µL compound solution or vehicle (30 sec at 1400 rpm on a shaker). Equilibration follows at room temperature, 250 rpm and for 30 min. The assay is starts by adding 10 µL of substrate solution (20 µM pantethine in 1 mM DTT, 0.0025% Brij-35, 50 mM HEPES, pH7.5) to each well, except for some blank wells which receive 10 mL substrate buffer (1 mM DTT, 0.0025% Brij-35, 50 mM HEPES, pH7.5) only. Samples are thoroughly shaken (30 sec, 1400 rpm) and reaction is allowed to take place at room temperature, 250 rpm and for 5 min. The reaction is stopped by addition of a vanin tool inhibitor in excess (BI-1 total conc. 10 µM). Centrifugation of the plate follows at 4° C., 665 G for 10 min. Then the blood plasma samples (100 µL) are transferred into another 96-deep-well plate and proteins are precipitated (5 min on ice) by adding 100 µL of ice cold precipitation solution (1 µM labelled pantothenic acid (di-β-alanine-13C6,15N2 calcium salt, Sigma, #705837) in acetonitrile). Afterwards the plate is centrifuged (4° C., 3220 G, 10 min) and supernatants (50 µL) are collected into another 96-deep-well plate and mixed (10 sec, 1400 rpm) with 150 µL ice cold formic acid (0.1%, Carl Roth GmbH+Co.KG, #CP03.1). The formation of pantothenic acid is detected by RapidFire Mass Spectrometry. A TripleQuad 6500+ (ABSciex, Germany) is equipped with an LC-1290 system, a RapidFire autosampler (Agilent, Germany) and a C18 cartridge Type C 12 µL (Agilent Cat #G9526-80000). Mobile phase A is consisting of 0.09% formic acid and 0.01% trifluoroacetic acid in water and mobile phase B of 0.09% formic acid and 0.01% trifluoroacetic acid in acetonitrile/methanol/water=47.5/47.5/5.

Synthesis of Tool Inhibitor BI-1:

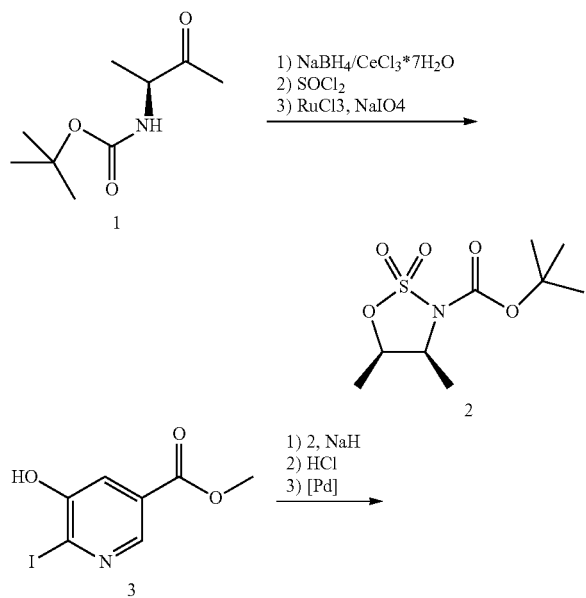

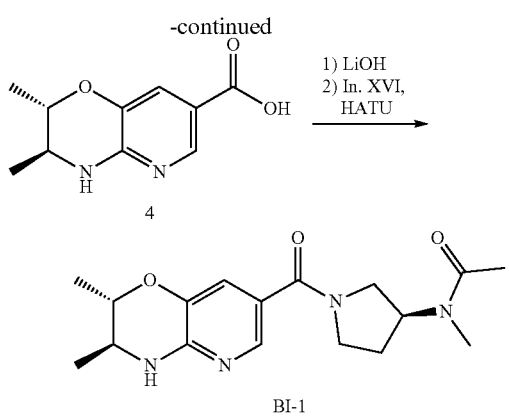

To 70 mL MeOH are added 5.40 g (28.8 mmol) ketone 1 (synthesis described in *Angew. Chem. Int. Ed.* 2010, 49, 6856) and 12.9 g (34.6 mmol) $CeCl_3*7 H_2O$. The reaction mixture is cooled to $-15°$ C. before 2.18 g (57.7 mmol) $NaBH_4$ are added portion wise. The reaction mixture is stirred for 3 h at 0° C. The reaction is quenched by the addition of saturated aq. $NH_4Cl$ solution and extracted with EtOAc. The organic layers are combined, dried over $Na_2SO_4$ and the solvent is removed in vacuo.

A stirred solution of 6.29 g (52.8 mmol) thionyl chloride in 50 mL acetonitrile is cooled to the $-50°$ C. and a solution of 4 g (21.1 mmol) in ACN of the above mentioned product is added drop wise. When addition completed then 258 mg (2.11 mmol) DMAP are added in one portion. The mixture is stirred for 15 min, keeping temperature below $-40°$ C., and then 8.36 g (106 mmol) dry pyridine are added, keeping external temperature at $-40°$ C. Stirring is continued for 1 h. EtOAc is added, stirred for 5 mins, suspension appeared (pyridine salt) which is filtered and washed with EtOAc. To the filtrate is added 12 mL saturated $Na_2HPO_4$ slowly. The resulting solution is stirred for 40 mins. Two layers are separated. The organic layer is washed with 10 mL 1M $NaHSO_4$ aqueous, dried over $Na_2SO_4$ and concentrated under reduced pressure. The crude compound is purified by column chromatography (silica gel, 8% EtOAc in hexane).

$C_9H_{17}NO_4S$ (M=235.3 g/mol)

ESI-MS: 258 $[M+Na]^+$ $R_f$ (TLC, silica gel) 0.4 (PE/EtOAc 3/1)

To a solution of 1.00 g (0.004 mol) of the above described product in 10,000 ml EtOAc are added 1.36 g (0.006 mol) $NaIO_4$ in 10 mL $H_2O$ Then 44 mg (0.2 mmol) $RuCl_3$ are added and the mixture is stirred at 0 to 15° C. for 12 h. The mixture is quenched with $H_2O$ (20 mL) and extracted with EtOAc. Then the organic phase is washed with brine (20 mL), dried over $Na_2SO_4$, filtered and concentrated to dryness. The residue is purified by column chromatography (silica gel, PE/EtOAc=10:1 to 3:1).

$C_9H_{17}NO_5S$ (M=251.3 g/mol)

ESI-MS: 252 $[M+H]^+$ $R_f$ (TLC, silica gel) 0.55 (PE/EtOAc 3/1)

4.00 g (14.3 mmol) methyl 5-hydroxy-6-iodopyridine-3-carboxylate are added to 40 ml of DMF. To this are added 602 mg (15.1 mmol) sodium hydride. After gas evolution, 5.40 g (21.5 mmol) are added and the reaction mixture is stirred at 75 C for 1.5 h. After cooling down to RT, the reaction mixture is diluted with EtOAc and rinsed with water. The organics are dried, filtered, and evaporated.

The residue is purified by column chromatography (silica gel, 0-5% MeOH/CH$_2$Cl$_2$).

C$_{16}$H$_{23}$IN$_2$O$_5$ (M=450.3 g/mol)
ESI-MS: 451 [M+H]$^+$ 5.00 g (11.1 mmol) of the above mentioned product are added to in 50 ml of MeOH and 10 ml of CH$_2$Cl$_2$. To this are added 50 ml of 4 M HCl in dioxane. After 3 h the volatiles are removed in vacuo and the residue used without further purification.

3.28 g (9.37 mmol) of the above mentioned product, 105 mg (0.47 mmol) Pd(OAc)$_2$, 0.33 g (0.56 mmol), 9,9-dimethyl-4,5-bis(diphenylphosphino)xanthene (0.33 g; 0.56 mmol; 6.00 mol %) and 9.16 g (28.1 mmol) cesium carbonate are added to 100 ml dioxane and the mixture is degassed thoroughly. The reaction mixture is stirred at 90° C. under argon for 4 h. The solids are filtered through a plug of Celite® and evaporated. The residue is purified by column chromatography (silica gel, 0-5% MeOH/CH$_2$Cl$_2$).

1.50 g (6.75 mmol) of the above mentioned product are added to 5 ml of MeOH and 70 ml of water. To this are added 323 mg (13.5 mmol) LiOH and the reaction mixture is stirred at 50° C. for 1 h. The reaction is filtered and the MeOH is removed in vacuo. The aqueous layer is neutralized with 1 M HCl. The solids are filtered and allowed to dry and used without further purification.

C$_{10}$H$_{12}$N$_2$O$_3$ (M=208.2 g/mol)
ESI-MS: 209 [M+H]$^+$
Rt (HPLC): 0.60 min (method A)

915 mg (4.39 mmol) of the above mentioned product are dissolved in 20 ml of DMF. To this are added 0.86 g (4.83 mmol) of intermediate XVI and 1.84 ml (13.2 mmol) TEA) followed by 1.84 g (4.83 mmol) HATU. The reaction mixture is stirred at RT for 16 h.

Volatiles are removed in vacuo and the residue is purified by column chromatography (Biotage KP-Nh cartridge, 0-10% MeOH/EtOAc).

C$_{17}$H$_{24}$N$_4$O$_3$ (M=332.4 g/mol)
ESI-MS: 333 [M+H]$^+$
Rt (HPLC): 0.63 min (method A)

Other features and advantages of the present invention will become apparent from the following more detailed examples which illustrate, by way of example, the principles of the invention

TABLE I

Biological properties of representatives of the present invention

| Ex. | Structure | VNN 1 IC$_{50}$ (nM) | HWB IC$_{50}$ (nM) |
|---|---|---|---|
| 1.1 | 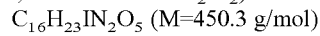 | 0.2 | 4.3 |
| 1.2 | 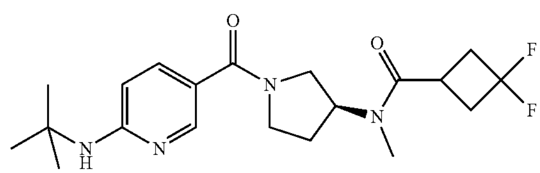 [SMILES: CN(C(=O)C1CC(F)(F)C1)[C@H]1CCN(C(=O)c2ccc(NC(C)(C)C)nc2)C1] | 0.2 | 3.6 |
| 1.3 | 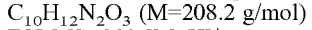 | 0.3 | 2.7 |
| 1.4 | 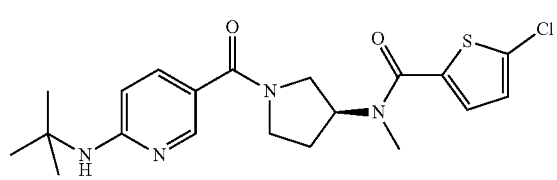 [SMILES: CN(C(=O)c1ccc(Cl)s1)[C@H]1CCN(C(=O)c2ccc(NC(C)(C)C)nc2)C1] | 0.3 | 25.2 |
| 1.5 | 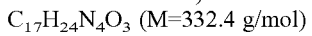 | 0.3 | 4.2 |

TABLE I-continued

Biological properties of representatives of the present invention

| Ex. | Structure | VNN 1 IC$_{50}$ (nM) | HWB IC$_{50}$ (nM) |
|---|---|---|---|
| 1.6 | 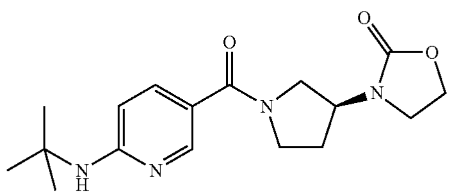 [SMILES: CC(C)(C)Nc1ccc(C(=O)N2CC[C@H](N3CCOC3=O)C2)cn1] | 0.3 | 4.0 |
| 1.7 | 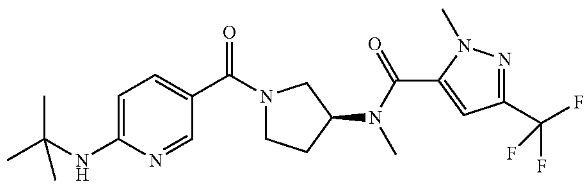 [SMILES: CN(C(=O)c1cc(C(F)(F)F)nn1C)[C@H]1CCN(C(=O)c2ccc(NC(C)(C)C)nc2)C1] | 0.3 | 5.0 |
| 1.8 | 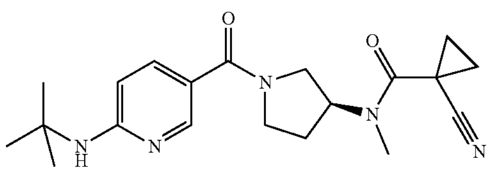 [SMILES: CN(C(=O)C1(C#N)CC1)[C@H]1CCN(C(=O)c2ccc(NC(C)(C)C)nc2)C1] | 0.3 | 5.8 |
| 1.9 | 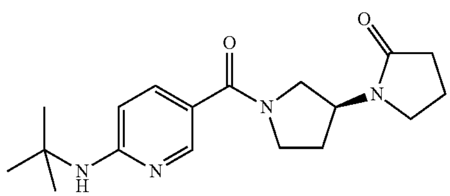 [SMILES: CC(C)(C)Nc1ccc(C(=O)N2CC[C@H](N3CCCC3=O)C2)cn1] | 0.4 | 3.1 |
| 1.10 | 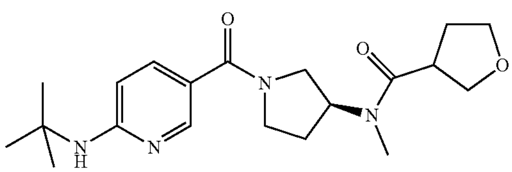 [SMILES: CN(C(=O)C1CCOC1)[C@H]1CCN(C(=O)c2ccc(NC(C)(C)C)nc2)C1] | 0.4 | |
| 1.11 | 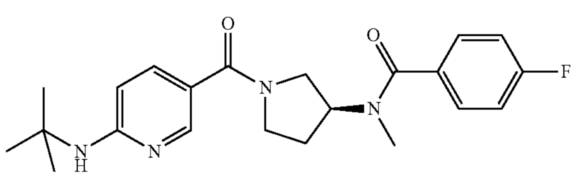 [SMILES: CN(C(=O)c1ccc(F)cc1)[C@H]1CCN(C(=O)c2ccc(NC(C)(C)C)nc2)C1] | 0.4 | 7.5 |
| 1.12 | 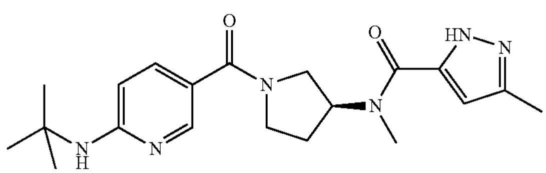 [SMILES: Cc1cc(C(=O)N(C)[C@H]2CCN(C(=O)c3ccc(NC(C)(C)C)nc3)C2)[nH]n1] | 0.4 | 9.7 |
| 1.13 | 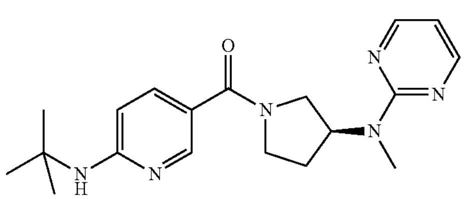 [SMILES: CN(c1ncccn1)[C@H]1CCN(C(=O)c2ccc(NC(C)(C)C)nc2)C1] | 0.4 | 12.6 |

TABLE I-continued

Biological properties of representatives of the present invention

| Ex. | Structure | VNN 1 IC$_{50}$ (nM) | HWB IC$_{50}$ (nM) |
| --- | --- | --- | --- |
| 1.14 | 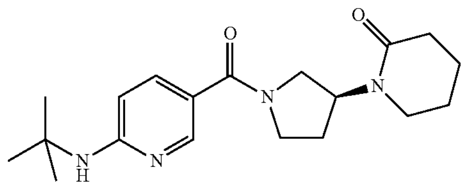 [SMILES: CC(C)(C)Nc1ccc(C(=O)N2CC[C@H](N3CCCCC3=O)C2)cn1] | 0.8 | 12.5 |
| 1.15 | 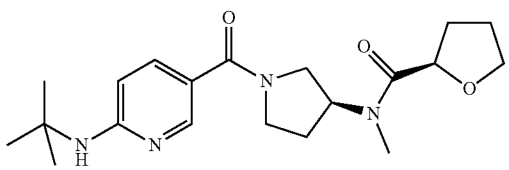 [SMILES: CN(C(=O)[C@H]1CCCO1)[C@H]1CCN(C(=O)c2ccc(NC(C)(C)C)nc2)C1] | 1.0 | |
| 1.16 | 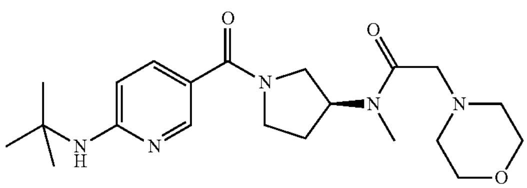 [SMILES: CN(C(=O)CN1CCOCC1)[C@H]1CCN(C(=O)c2ccc(NC(C)(C)C)nc2)C1] | 1.3 | |
| 2.1 | 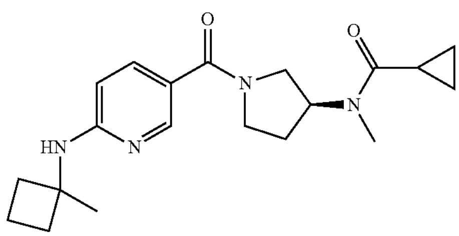 [SMILES: CN(C(=O)C1CC1)[C@H]1CCN(C(=O)c2ccc(NC3(C)CCC3)nc2)C1] | 0.3 | 4.6 |
| 2.2 | 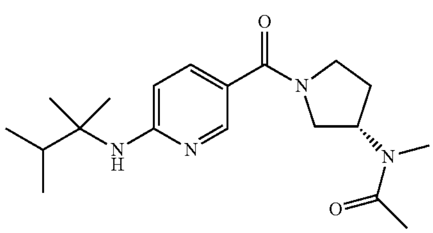 [SMILES: CC(=O)N(C)[C@H]1CCN(C(=O)c2ccc(NC(C)(C)C(C)C)nc2)C1] | 0.4 | 7.7 |
| 2.3 | 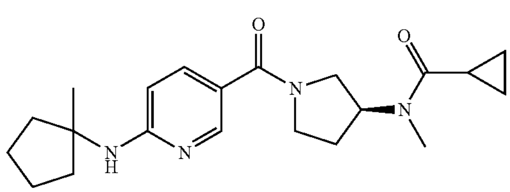 [SMILES: CN(C(=O)C1CC1)[C@H]1CCN(C(=O)c2ccc(NC3(C)CCCC3)nc2)C1] | 0.7 | |
| 2.4 | 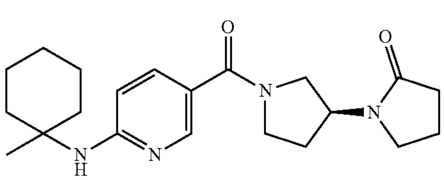 [SMILES: CC1(Nc2ccc(C(=O)N3CC[C@H](N4CCCC4=O)C3)cn2)CCCCC1] | 1.7 | |

TABLE I-continued

Biological properties of representatives of the present invention

| Ex. | Structure | VNN 1 IC$_{50}$ (nM) | HWB IC$_{50}$ (nM) |
|---|---|---|---|
| 2.5 | 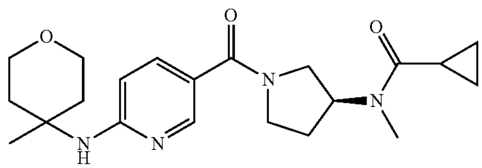 [SMILES: CN(C(=O)C1CC1)[C@H]1CCN(C(=O)c2ccc(NC3(C)CCOCC3)nc2)C1] | 7.3 | |
| 2.6 | 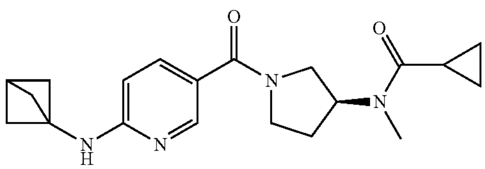 [SMILES: CN(C(=O)C1CC1)[C@H]1CCN(C(=O)c2ccc(NC34CC(C3)C4)nc2)C1] | 0.4 | 9.2 |
| 3.1 | 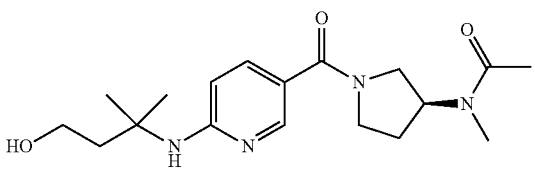 [SMILES: CC(=O)N(C)[C@H]1CCN(C(=O)c2ccc(NC(C)(C)CCO)nc2)C1] | 0.2 | 1.6 |
| 3.2 | 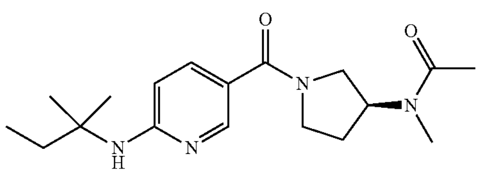 [SMILES: CCC(C)(C)Nc1ccc(C(=O)N2CC[C@H](N(C)C(C)=O)C2)cn1] | 0.2 | 3.1 |
| 3.3 | 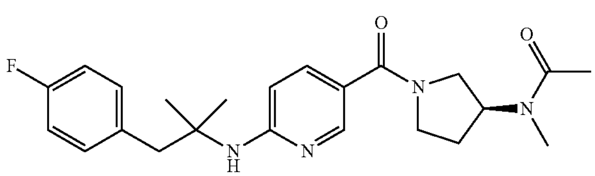 [SMILES: CC(=O)N(C)[C@H]1CCN(C(=O)c2ccc(NC(C)(C)Cc3ccc(F)cc3)nc2)C1] | 0.4 | 8.7 |
| 3.4 | 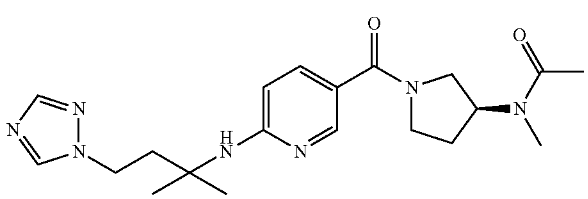 [SMILES: CC(=O)N(C)[C@H]1CCN(C(=O)c2ccc(NC(C)(C)CCn3cncn3)nc2)C1] | 2.1 | |
| 4.1 | 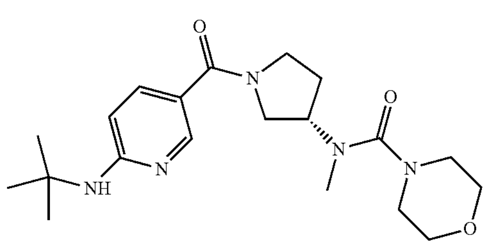 [SMILES: CN(C(=O)N1CCOCC1)[C@H]1CCN(C(=O)c2ccc(NC(C)(C)C)nc2)C1] | 0.3 | 3.2 |

TABLE I-continued

Biological properties of representatives of the present invention

| Ex. | Structure | VNN 1 IC$_{50}$ (nM) | HWB IC$_{50}$ (nM) |
|---|---|---|---|
| 4.2 | 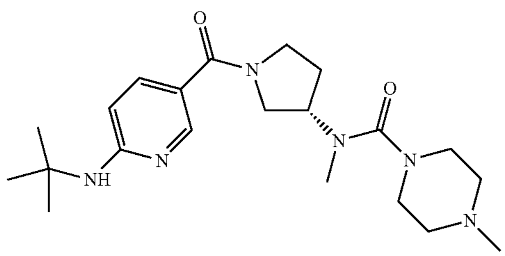 [SMILES: CN1CCN(C(=O)N(C)[C@H]2CCN(C(=O)c3ccc(NC(C)(C)C)nc3)C2)CC1] | 1.2 | |
| 5.1 | 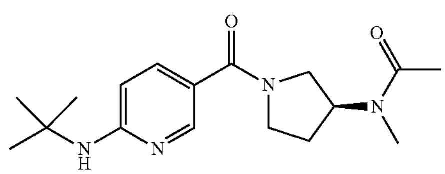 [SMILES: CC(=O)N(C)[C@H]1CCN(C(=O)c2ccc(NC(C)(C)C)nc2)C1] | 0.5 | 3.2 |
| 5.2 | 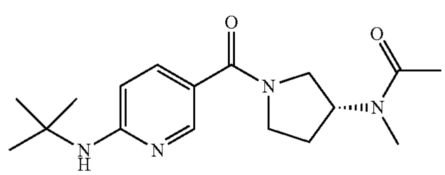 [SMILES: CC(=O)N(C)[C@@H]1CCN(C(=O)c2ccc(NC(C)(C)C)nc2)C1] | | 267 |
| 6 | 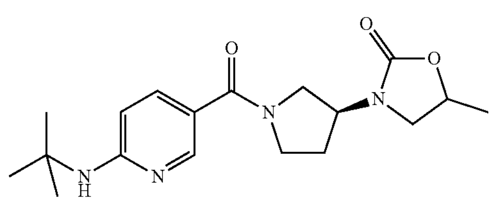 [SMILES: CC1CN([C@H]2CCN(C(=O)c3ccc(NC(C)(C)C)nc3)C2)C(=O)O1] | 1.6 | |
| 7* | 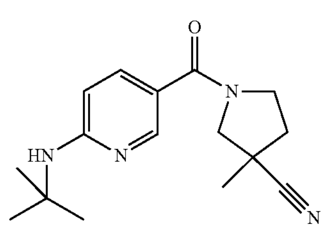 [SMILES: CC1(C#N)CCN(C(=O)c2ccc(NC(C)(C)C)nc2)C1] | 0.3 | 3.9 |
| 8 | 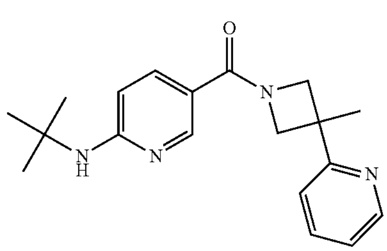 [SMILES: CC(C)(C)Nc1ccc(C(=O)N2CC(C)(c3ccccn3)C2)cn1] | 0.3 | 2.7 |

*Enantiomerically pure compound. Absolut configuration not determined.

The invention claimed is:

1. A compound of the formula I, or a pharmaceutically acceptable salt thereof,

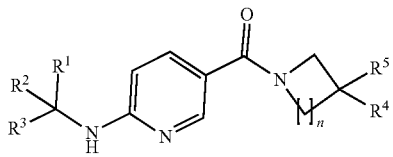

I wherein
n denotes 1 or 2;
$R^1$, $R^2$ and $R^3$ are independently from each other selected from the group consisting of $C_{1-4}$-alkyl optionally substituted by hydroxy, $CH_3$—O—, $CH_3$—$SO_2$—, Phenyl-$CH_2$— optionally substituted by 1 to 3 halogen atoms and 5-6 membered heteroaryl-$C_{1-2}$-alkyl-;
or
$R^2$ and $R^3$ together form a 3-6 membered carbocycle or 4-6 membered heterocyclyl containing one heteroatom selected from the group consisting of N and O;
or
$R^1$, $R^2$ and $R^3$ together may form or a bicyclic 5-8 membered carbocycle or a bicyclic 6-8 membered heterocyclyl containing one heteroatom selected from the group consisting of N and O;
wherein in the definition of $R^1$, $R^2$ and $R^3$ mentioned alkyl, cycloalkyl, heteroaryl and heterocyclyl are optionally substituted by 1 to 3 halogen atoms;
$R^4$ denotes $R^{4.1}R^{4.2}N$—, 5-6 membered heteroaryl, NC— or 5-6 membered heterocyclyl;
or
$R^4$ denotes a group of formula $R^{4.a}$ or $R^{4.b}$

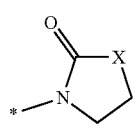

$R^{4.a}$

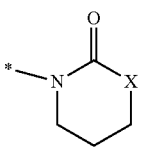

$R^{4.b}$ wherein
X denotes $CH_2$, —$NR^X$ or O;
wherein $R^X$ denotes H or $C_{1-3}$-alkyl;
$R^{4.a}$ and $R^{4.b}$ independently from each other are optionally substituted by methyl;
$R^{4.1}$ is selected from the group consisting of $C_{1-4}$-alkyl-CO— optionally substituted by 1-3 F-atoms, $C_{3-4}$-cycloalkyl or $C_{1-2}$-alkoxy, $C_{3-5}$-cycloalkyl-CO— substituted with $R^{4.1.1}$ and $R^{4.1.2}$, 4-6 membered heterocyclyl-CO— substituted with $R^{4.1.3}$ and $R^{4.1.4}$, 4-6 membered heterocyclyl-$CH_2$—CO—, 5-6 membered heteroaryl-CO— optionally substituted by 1 halogen atom, $H_3C$—O— or 1 to 2 methyl, phenyl-CO— substituted with $R^{4.1.5}$ and $R^{4.1.6}$, ($C_{1-3}$-alkyl)($C_{1-3}$-alkyl)N—CO— and 5-6 membered heteroaryl;

wherein
$R^{4.1.1}$, $R^{4.1.2}$ independently from each other are selected from the group consisting of H, —$CH_3$, F, $CF_3$ and CN;
$R^{4.1.3}$, $R^{4.1.6}$ independently from each other are selected from the group consisting of H, —$CH_3$, F, $CF_3$ and —CN;
$R^{4.1.5}$, $R^{4.1.6}$ independently from each other are selected from the group consisting of H, —$CH_3$, F, $CF_3$ and —CN;
$R^{4.2}$ is selected from the group consisting of H, $C_{1-4}$-alkyl, $C_{3-4}$-cycloalkyl, $C_{3-4}$-cycloalkyl-$C_{1-2}$-alkyl- and phenyl-$C_{1-2}$-alkyl-;
wherein in the definition of $R^{4.2}$ mentioned alkyl, cycloalkyl and phenyl are optionally substituted by 1-3 F-atoms or one $C_{1-2}$-alkyl-O—;
$R^5$ denotes H or $C_{1-2}$-alkyl;
or
$R^4$ and $R^5$ together form 4-6 membered heterocyclyl containing 1 heteroatom selected from the group consisting of N and O;
or a pharmaceutically acceptable salt thereof.

2. The compound according to claim 1,
wherein
n denotes 1,
or a pharmaceutically acceptable salt thereof.

3. A compound according to claim 1,
wherein
n denotes 2,
or a pharmaceutically acceptable salt thereof.

4. The compound according to claim 1, wherein
$R^1$ denotes methyl,
or a pharmaceutically acceptable salt thereof.

5. The compound according to claim 1, wherein
$R^2$ denotes methyl,
or a pharmaceutically acceptable salt thereof.

6. The compound according to claim 1, wherein
$R^3$ denotes $C_{1-3}$-alkyl optionally substituted by hydroxy
or a pharmaceutically acceptable salt thereof.

7. The compound according to claim 1, wherein
$R^2$ and $R^3$ together form a 4-6 membered carbocycle or 6-membered heterocyclyl
containing one oxygen atom,
or a pharmaceutically acceptable salt thereof.

8. The compound according to claim 1, wherein
$R^4$ is selected from the group consisting of $R^{4.1}R^{4.2}N$—, pyridinyl and NC—;
or
$R^4$ denotes a group of formula $R^{4.a}$ or $R^{4.b}$

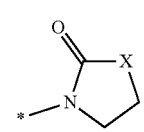

$R^{4.a}$

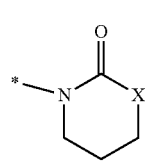

$R^{4.b}$ wherein
X denotes $CH_2$ or O;
$R^{4.a}$ and $R^{4.b}$ independently from each other are optionally substituted by methyl,
$R^{4.1}$ is selected from the group consisting of $C_{1-4}$-alkyl-CO—, $C_{3-4}$-cycloalkyl-CO— substituted with $R^{4.1.1}$ and $R^{4.1.2}$, 5-6 membered heteroaryl-CO— substituted with $R^{4.1.3}$ and $R^{4.1.4}$, 6 membered heterocyclyl-$CH_2$—CO—, 5 membered heteroaryl-CO— optionally substituted by 1 halogen atom, phenyl-CO— substituted with $R^{4.1.5}$ and $R^{4.1.6}$ and 6 membered heteroaryl;
wherein
$R^{4.1.1}$, $R^{4.1.2}$ independently from each other are selected from the group consisting of H, —$CH_3$, F, $CF_3$ and —CN;
$R^{4.1.3}$, $R^{4.1.4}$ independently from each other are selected from the group consisting of H, —$CH_3$, F, $CF_3$ and —CN;
$R^{4.1.5}$, $R^{4.1.6}$ independently from each other are selected from the group consisting of H, —$CH_3$, F, $CF_3$ and —CN;
$R^{4.2}$ denotes methyl;
or a pharmaceutically acceptable salt thereof.
9. The compound according to claim 1, wherein
$R^5$ denotes H or methyl;
or a pharmaceutically acceptable salt thereof.
10. The compound according to claim 1, wherein
n denotes 1 or 2;
$R^1$ denotes methyl;
$R^2$ denotes methyl;
$R^3$ denotes $C_{1-3}$-alkyl optionally substituted by hydroxyl;
or
$R^2$ and $R^3$ together form a 4-6 membered carbocycle or a 6-membered heterocyclyl containing one oxygen atom;
$R^4$ is selected from the group consisting of $R^{4.1}R^{4.2}N$—, pyridinyl and NC—;
or
$R^4$ denotes a group of formula $R^{4.a}$ or $R^{4.b}$;

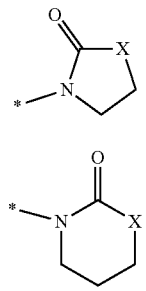

wherein
X denotes $CH_2$ or O;
$R^{4.a}$ and $R^{4.b}$ independently from each other are optionally substituted by methyl,
$R^{4.1}$ is selected from the group consisting of $C_{1-4}$-alkyl-CO—, $C_{3-5}$-cycloalkyl-CO— substituted with $R^{4.1.1}$ and $R^{4.1.2}$, 4-6 membered heterocyclyl-CO— substituted with $R^{4.1.3}$ and $R^{4.1.4}$, 6 membered heterocyclyl-$CH_2$—CO—, 5-6 membered heteroaryl-CO— optionally substituted by 1 halogen atom, phenyl-CO— substituted with $R^{4.1.5}$ and $R^{4.1.6}$ and 6 membered heteroaryl containing 1 or 2 N-atoms;

wherein
$R^{4.1.1}$, $R^{4.1.2}$ independently from each other are selected from the group consisting of H, F and —CN;
$R^{4.1.3}$, $R^{4.1.4}$ independently from each other are selected from the group consisting of H, —$CH_3$ and $CF_3$;
$R^{4.1.5}$, $R^{4.1.6}$ independently from each other are selected from the group consisting of H and F;
$R^{4.2}$ denotes methyl;
$R^5$ denotes H or methyl;
or a pharmaceutically acceptable salt thereof.

11. The compound of formula I according to claim 1 selected from the group consisting of examples 1.2, 1.3, 1.5, 1.6, 1.8, 1.9, 1.11, 3.2, 5.1 and 7.1;

Ex. 1.2
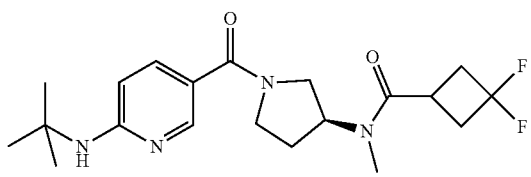

Ex. 1.3
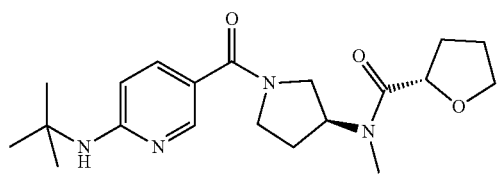

Ex. 1.5
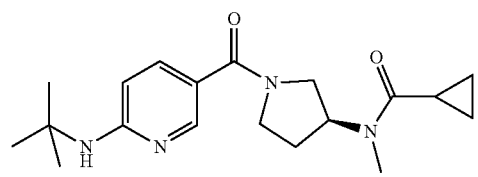

Ex. 1.6
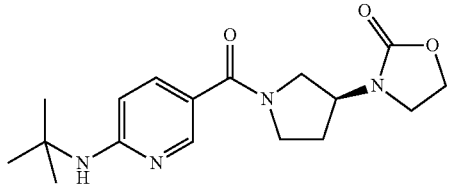

Ex. 1.8
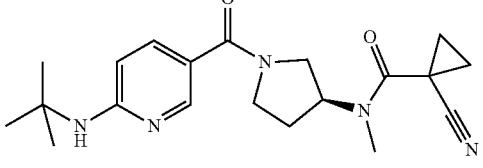

Ex. 1.9
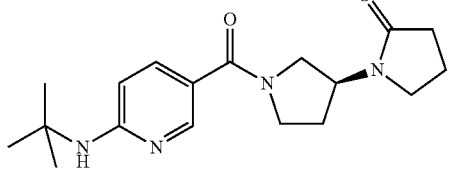

-continued

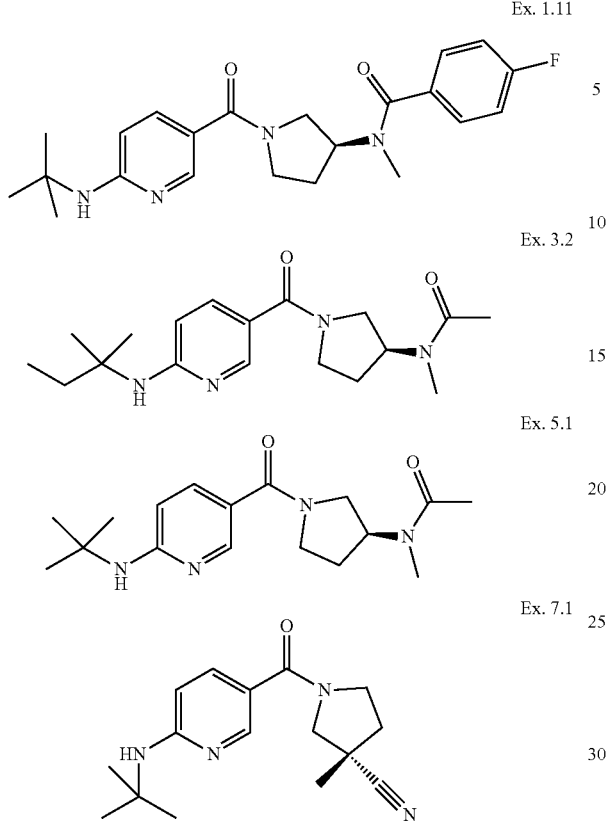

or a pharmaceutically acceptable salt thereof.

12. A compound of formula IB according to claim 1,

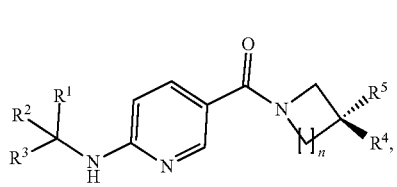

or a pharmaceutically acceptable salt thereof.

13. A pharmaceutical composition comprising a therapeutically effective amount of at least one compound of formula I according to claim 1 or a pharmaceutically acceptable salt thereof and one or more pharmaceutically acceptable excipients.

14. A method of using the compound according to claim 1 for treating a patient suffering from Crohn's disease, ulcerative colitis, atopic dermatitis, systemic sclerosis, Non-Alcoholic Steatohepathitis (NASH), psoriasis, chronic kidney disease, chronic obstructive pulmonary disease, idiopathic pulmonary fibrosis, rheumatoid arthritis, scleroderma, asthma, allergic rhinitis, allergic eczema, juvenile rheumatoid arthritis, juvenile idiopathic arthritis, graft versus host disease, psoriatic arthritis, Hyperlipidemia, colorectal cancer or pancreatic cancer related new onset diabetes.

15. A pharmaceutical composition comprising additionally to a compound of formula I according to claim 1, a pharmaceutically active compound selected from the group consisting of an immunomodulatory agent, anti-inflammatory agent or a chemotherapeutic agent.

16. A compound of formula:

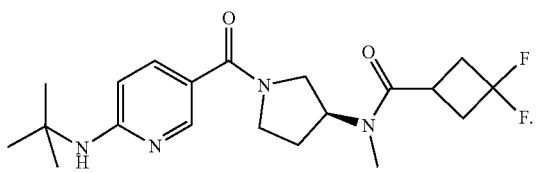 [SMILES: CN(C(=O)C1CC(F)(F)C1)[C@H]1CCN(C(=O)c2ccc(NC(C)(C)C)nc2)C1]

17. A compound of formula:

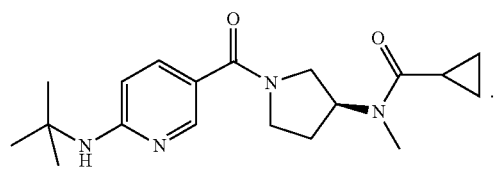 [SMILES: CN(C(=O)C1CC1)[C@H]1CCN(C(=O)c2ccc(NC(C)(C)C)nc2)C1 ; "."]

18. A compound of formula:

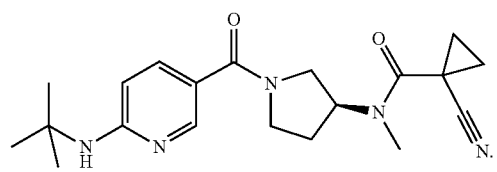 [SMILES: CN(C(=O)C1(C#N)CC1)[C@H]1CCN(C(=O)c2ccc(NC(C)(C)C)nc2)C1]

19. A compound of formula:

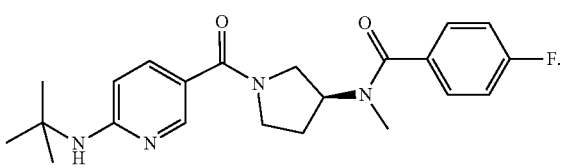 [SMILES: CN(C(=O)c1ccc(F)cc1)[C@H]1CCN(C(=O)c2ccc(NC(C)(C)C)nc2)C1]

20. A compound of formula:

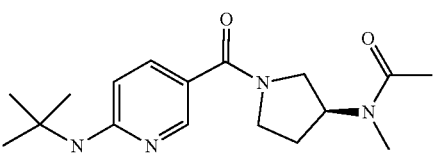

21. A compound of formula:

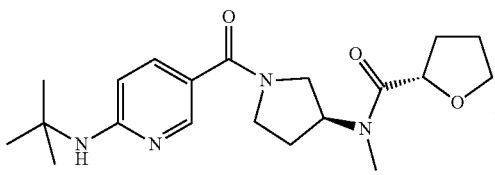 [SMILES: CN(C(=O)[C@@H]1CCCO1)[C@H]1CCN(C(=O)c2ccc(NC(C)(C)C)nc2)C1]

22. A compound of formula:

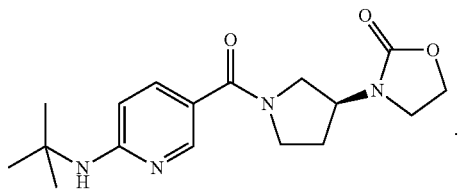 [SMILES: CC(C)(C)Nc1ccc(C(=O)N2CC[C@H](N3CCOC3=O)C2)cn1]

23. A compound of formula:

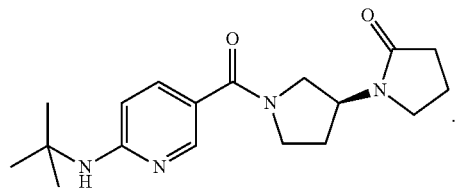 [SMILES: CC(C)(C)Nc1ccc(C(=O)N2CC[C@H](N3CCCC3=O)C2)cn1]

24. A compound formula:

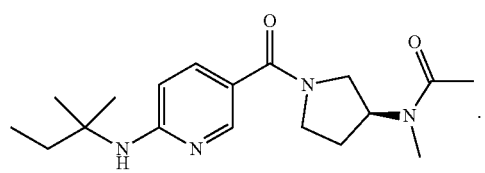 [SMILES: CCC(C)(C)Nc1ccc(C(=O)N2CC[C@H](N(C)C(C)=O)C2)cn1]

25. A compound of formula:

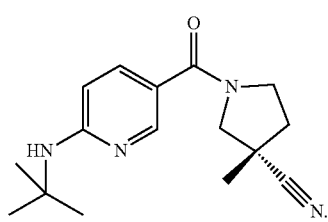 [SMILES: CC(C)(C)Nc1ccc(C(=O)N2CC[C@](C)(C#N)C2)cn1]

26. A compound of formula:

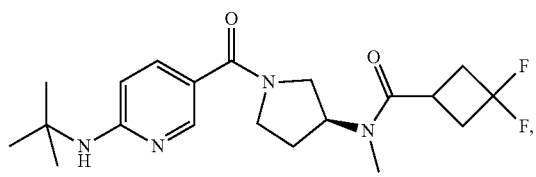 [SMILES: CN(C(=O)C1CC(F)(F)C1)[C@H]1CCN(C(=O)c2ccc(NC(C)(C)C)nc2)C1]

or a pharmaceutically acceptable salt thereof.

27. A compound of formula:

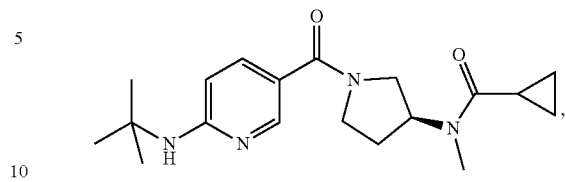

or a pharmaceutically acceptable salt thereof.

28. A compound of formula:

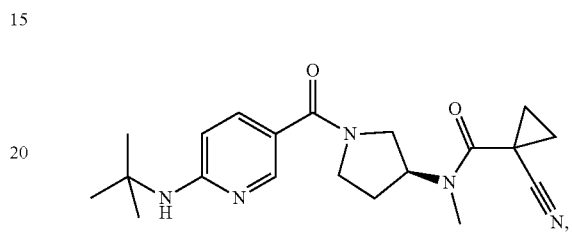

or a pharmaceutically acceptable salt thereof.

29. A compound of formula:

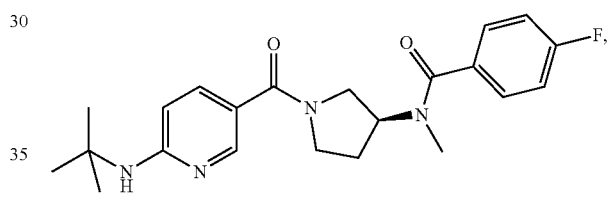

or a pharmaceutically acceptable salt thereof.

30. A compound of formula:

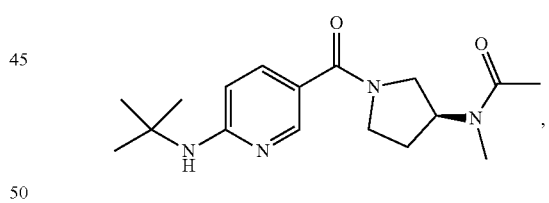

or a pharmaceutically acceptable salt thereof.

31. A compound of formula:

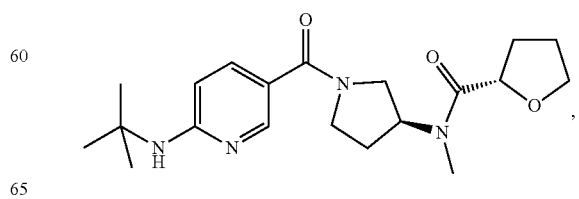

or a pharmaceutically acceptable salt thereof.

32. A compound of formula:
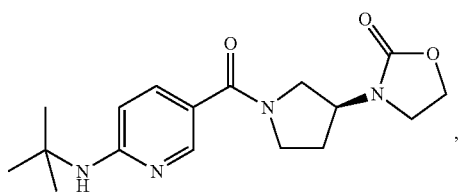 [SMILES: CC(C)(C)Nc1ccc(C(=O)N2CC[C@H](N3CCOC3=O)C2)cn1]
or a pharmaceutically acceptable salt thereof.
33. A compound of formula:
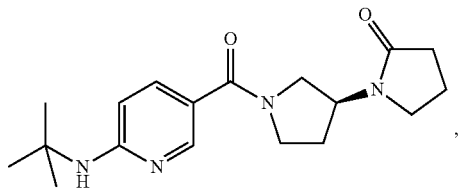
or a pharmaceutically acceptable salt thereof.
34. A compound of formula:
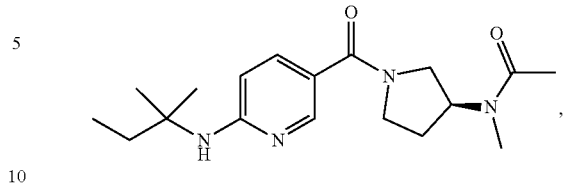
or a pharmaceutically acceptable salt thereof.
35. A compound of formula:
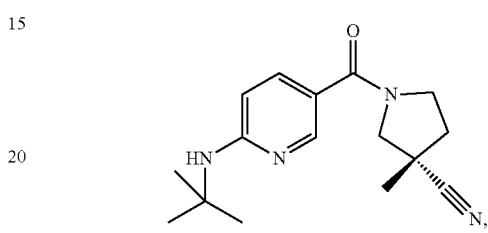
or a pharmaceutically acceptable salt thereof.
* * * * *

UNITED STATES PATENT AND TRADEMARK OFFICE
CERTIFICATE OF CORRECTION

PATENT NO. : 11,078,182 B2
APPLICATION NO. : 16/699799
DATED : August 3, 2021
INVENTOR(S) : Fleck et al.

Page 1 of 1

It is certified that error appears in the above-identified patent and that said Letters Patent is hereby corrected as shown below:

In the Claims

In Column 74, replace the compound at Lines 49-55 with the following compound:

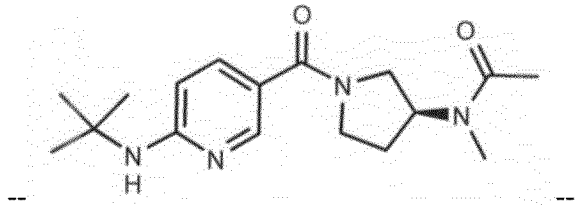

Signed and Sealed this
Fifth Day of April, 2022

Drew Hirshfeld
*Performing the Functions and Duties of the
Under Secretary of Commerce for Intellectual Property and
Director of the United States Patent and Trademark Office*